(12) United States Patent
Achanath et al.

(10) Patent No.: US 8,501,153 B2
(45) Date of Patent: *Aug. 6, 2013

(54) ACTIVE ENANTIOMER

(75) Inventors: Radha Achanath, Bangalore (IN);
Srinath Balaji, Bangalore (IN); Afsal M. Kadavilpparampu Mohamed, Bangalore (IN); Umamaheshwar Mokkapati, Bangalore (IN); Steven Fairway, Oslo (NO); Dimitrios Mantzilas, Oslo (NO); Dennis O'Shea, Amersham (GB); William John Trigg, Amersham (GB); Harry John Wadsworth, Amersham (GB); Joanna Marie Passmore, Amersham (GB); Bo Shan, Shanghai (CN)

(73) Assignee: GE Healthcare Limited, Buckinghamshire (GB)

(*) Notice: Subject to any disclaimer, the term of this patent is extended or adjusted under 35 U.S.C. 154(b) by 93 days.

This patent is subject to a terminal disclaimer.

(21) Appl. No.: 12/880,218

(22) Filed: Sep. 13, 2010

(65) Prior Publication Data

US 2011/0070161 A1    Mar. 24, 2011

Related U.S. Application Data

(63) Continuation-in-part of application No. PCT/EP2010/053998, filed on Mar. 26, 2010.

(60) Provisional application No. 61/164,131, filed on Mar. 27, 2009.

(30) Foreign Application Priority Data

Aug. 10, 2010 (IN) ........................... 1824/DEL/2010

(51) Int. Cl.
*A61K 51/00* (2006.01)
*A61K 36/14* (2006.01)

(52) U.S. Cl.
USPC .......... 424/1.11; 424/1.89; 422/159; 548/448

(58) Field of Classification Search
None
See application file for complete search history.

(56) References Cited

U.S. PATENT DOCUMENTS 6,281,355 B1 * 8/2001 Nakazato et al. ............... 544/14

FOREIGN PATENT DOCUMENTS

| EP | 0248734 | 12/1987 |
|---|---|---|
| WO | 00/44751 | 8/2000 |
| WO | WO 2007057705 A1 * | 5/2007 |
| WO | 2010/109007 | 9/2010 |

OTHER PUBLICATIONS

Zhang et al. Bioorg. Med.Chem. Lett. 2003, 201-204.*
Waterhouse Mol. Imag. Biol. 2003, 5, 376-389.*

Richard B. Banati et al; "Long-Term Trans-Synaptic Glial Responses in the Human Thalamus After Peripheral Nerve Injury". Neuroreport, Nov. 16, 2001, vol. 12, No. 16, pp. 3439-3442.

R.B. Banati et al; "Positron Emission Tomography Imaging of Activated Microglia in Vivo in Rasmussen'S Encephalitis". American Academy of Neurology 1999; 53; 2199-2203.

Gerhard W. Goerres et al; "Imaging Cerebral Vasculitis in Refractory Epilepsy Using [11C] (R)-PK11195 Positron Emission Tomography". Apr. 2001, American J. Roentgenol; 176 (4) p. 1016-1018.

Annachiara Cagnin et al; "In Vivo Visualization of Activated Glia by [11 C] (R)-PK11195-PET Following Herpes Encephalitis Reveals Projected Neuronal Damage Beyond the Primary Focal Lesion". Oxford University Press (2001) 124, pp. 2014-2027.

Alexander Gerhard et al; "In Vivo Imaging of Microglial Activation With [11 C] (R)-PK11195 PET in Idiopathic Parkinson'S Disease". Neurobiology of Disease 2006, p. 404-412.

Yasuomi Ouchi et al; "Microglial Activation and Dopamine Terminal Loss in Early Parkinson'S Disease". American Neurological Association; 2005, 57 p. 168-175.

Alexander Gerhard et al; "In Vivo Imaging of Microglial Activation With [11 C] (R)-PK11195 PET in Corticobasal Degeneration". Movement Disorders, 2004,vol. 19, No. 10.

A. Gerhard et al; "[11 C] (R) PK11195 PET Imaging of Microglial Activation in Multiple System Atrophy". Neurology 2003; 61; pp. 686-689.

N. Pavese et al; "Microglial Activation Correlates With Severity in Huntington Disease; A Clinical and PET Study". Neurology 2006; 66; pp. 1638-1643.

Yen F. Tai et al; "Imaging Microglial Activation in Huntington's Disease". Brain Reseach Bulletin 72 (2007) pp. 148-151.

Annachiara Cagnin et al; "In-Vivo Measurement of Activated Microglia in Dementia". The Lancet, vol. 358, Aug. 11, 2001. pp. 461-467.

Fumihiko Yasuno et al; "Increased Binding of Peripheral Benzodiazepine Receptor in Alzheimer's Disease Measured by Positron Emission Tomography With [11 C] DAA1106". Society of Biological Psychiatry 2008; 64; pp. 835-841.

Alexander Gerhard et al; "Evolution of Microglial Activation in Patients After Ischemic Stroke; A [11 C] (R)-PK11195 PET Study". Neuroimage 24 (2005) pp. 591-595.

(Continued)

*Primary Examiner* — Michael G Hartley
*Assistant Examiner* — Sean R Donohue

(57) ABSTRACT

The present invention provides a PET tracer that has improved properties for imaging the peripheral benzodiazepine receptor (PBR) as compared with known such PET tracers. The present invention also provides a precursor compound useful in the preparation of the PET tracer of the invention and methods for the preparation of said precursor compound and said PET tracer. Also provided by the present invention is a radiopharmaceutical composition comprising the PET tracer of the invention. Methods for using the PET tracer and the radiopharmaceutical composition are also provided.

20 Claims, 10 Drawing Sheets

OTHER PUBLICATIONS

Anny Sauvageau et al; "Increased Expression of "Peripheral-Type" Benzodiazepine Receptors in Human Temporal Lobe Epilepsy: Implications for PET Imaging of Hippocampal Sclerosis". Metabolic Brain Disease, Vol. 17, No. 1, Mar. 2002.

Ajay Kumar et al; "Epilepsy Surgery in a Case of Encephalitis; Use of 11C-PK11195 Positron Emission Tomography". Pediatric Neurology 2008; 38; pp. 439-442.

Hiroshi Toyama et al; "In Vivo Imaging of Microglial Activation Using a Peripheral Benzodiazepine Receptor Ligand: [11 C] PK-11195 and Animal PET Following Ethanol Injury in Rat Striatum". Ann Nucl Med, Feb. 19 2008, pp. 417-424.

Sriram Venneti et al;"The High Affinity Peripheral Benzodiazepine Receptor Ligand DAA1106 Binds Specifically to Microglia in a Rat Model of Traumatic Brain Injury: Implications for PET Imaging". Experimental Neurology 207, (2007) pp. 118-127.

Julia Lehmann et al; "Peripheral Benzodiazepine Receptors in Cerebral Cortex, but not in Internal Organs, are Increased Following Inescapable Stress and Subsequent Avoidance/Escape Shuttle-Box Testing". Brain Research 851 (1999) p. 141-147.

Larry Junck et al; "PET Imaging of Human Gliomas With Ligands for the Peripheral Benzodiazepine Binding Site". American Neurological Association, 1989,26, pp. 752-758.

Makoto Tsuda et al; "Neuropathic Pain and Spinal Microglia; A Big Problem From Molecules in 'Small' Glia". Trends in Neurosciences, vol. 28, No. 2, Feb. 2005 pp. 101-107.

Howard M. Branley et al; "PET Scanning of Macrophages in Patients With Scleroderma Fibrosing Alveolitis". Nuclear Medicine and Biology, 35, (2008) pp. 901-909.

Conny J. Van Der Laken et al; "Noninvasive Imaging of Macrophages in Rheumatoid Synovitis Using 11 C-(R)-PK11195 and Positron Emission Tomography". Arthritis & Rheumatism, vol. 58, No. 11, Nov. 11 2008, pp. 3350-3355.

Pascal F. Durrenberger et al; "Cyclooxygenase-2 (COX-2) in Injured Human Nerve and a Rat Model of Nerve Injury". Journal of the Peripheral Nervous System 9; (2004) pp. 15-25.

Yota Fujimura et al; "Increased Peripheral Benzodiazepine Receptors in Arterial Plaque of Patients with Atherosclerosis: An Autoradiographic Study With [3H] PK 11195". Atherosclerosis 201, (2008) pp. 108-111.

Helena Miettinen et al; "Expression of Peripheral-Type Benzodiazepine Receptor and Diazepam Binding Inhibitor in Human Astrocytomas: Relationship to Cell Proliferation". Cancer Research 55, Jun. 15, 1995, pp. 2691-2695.

Gunnar Antoni et el;"Aspects on the Synthesis of 11C-Labelled Compounds". Handbook of Radiopharmaceuticals; Radiochemistry and Applications, 2003, ISBN: 0-471-49560-3.

M.R. Turner et al; "Evidence of Widespread Cerebral Microglial Activation in Amyotrophic Lateral Sclerosis: An [11C] (R)-PK11195 Positron Emission Tomography Study". Neurobiology of Disease 15, (2004) pp. 601-609.

Helena Miettinen et al; "Expression of Peripheral-Type Benzodiazephine Receptor and Diazepam Binding Inhibitor in Human Astrocytomas: Relationship to Cell Proliferation". Cancer Research; 55(12) pp. 2691-2695, Date: 1995.

Han et al; Expression of Peripheral Benzodiazepine Receptor (PBR) in Human Tumors: Relationship to Breast, Colorectal, and Prostate Tumor Progression. Journal of Receptors and Signal Transduction, 2003, vol. 23, Nos. 2&3, pp. 225-238.

Debruyne et al; "Semiquantification of the Peripheral-Type Benzodiazepine Ligand [11C] PK11195 in Normal Human Brain and Application I Multiple Sclerosis Patients".Acta Neurol Belg; 2002, 102 (3); pp. 127-135.

Jones et al; "In Vivo Assessment of Lung Inflammatory Cell Activity in Patients With COPD and Asthma". 2003, Eur Respir J; 21 (4) pp. 567-573.

Faggioli et al; "Increase in Peripheral Benzodiazepine Receptors on Monocytes in Fibromyalgia" 2004, Rheumatorlogy/ 43 (10) pp. 1224-1225.

Deane et al; "Targeted Imaging of Colonic Tumors in SMAD3 Mice Discriminates Cancer and Inflammation"2007, Mol Cancer Res; 5 (4) pp. 341-349.

Okubu et al; "Design, Synthesis, and Structure-Activity Relationships of Novel Tetracyclic Compounds as Peripheral Benzodiazepine Receptor Ligands" 2004, Bioorganic & Medicinal Chemistry 12, pp. 3569-3580.

Kozikowski A P et al; "Chemistry, Binding Affinities, and Behavioral Properties of a New Class of 'Antineophobic' Mitochondrial DBI Receptor Complex (mDRC) Ligands". Journal of Medicinal Chemistry, 1993, US, vol. 36, No. 20, pp. 2908-2920.

Taketoshi Okubo et al; "Design, Synthesis, and Structure-Activity Relationships of Novel Tetracyclic Compounds as Peripheral Benzodiazepine Receptor Ligands" Bioorganic & Medicinal Chemistry, Pergamon, GB Jan. 1, 2004, vol. 12, pp. 3569-3580.

Da Settimo, F et al; "Isosteric Replacement of the Indole Nucleus by Benzothiophene and Benzofuran in a Series of Indolylglyoxylylamine Derivatives With Partial Agonist Activity at the Benzodiazepine Receptor" European Journal of Medicinal Chemistry, Editions Scientifique Elsevier, Paris, FR, Jan. 1, 1996, vol. 31, No. 12, pp. 951-956.

Da Settimo A et al; "Synthesis of 3-(2'-Furoyl) Indole Derivatives as Potential New Ligands at the Benzodiazepine Receptor, Structurally More Restrained Analogues of Indoleglyoxylylamides" Farmaco 1995, vol. 50, No. 5, p. 311-320.

Homes T P et al; "Synthesis and In Vitro Binding of N,N-Dialkyl-2-Phenylindo1-3YL-Glyoxylamides for the Peripheral Benzodiazepine Binding Sites" Bioorganic & Medicinal Chemistry, Pergamon GB, Jun. 1, 2006, vol. 14, No. 11, pp. 3938-3946.

Bennacef I et al; "Synthesis and Receptor Binding Studies of Halogenated N,N-Dialkylel-(2-Phenyl-1H-Indol-3-YL) Glyoxylamides to Visualize Peripheral Benzodiazepine Receptors With Spect or PET". Bioorganic & Medicinal Chemistry, Pergamon GB, Nov. 15 2006, vol. 14, No. 22, pp. 7582-7591.

Primofiore G et al; "N, N-Dialkyl-2-Phenylindol-3-Ylglyoxylamides, a New Class of Potent and Selective Ligands at the Peripheral Renzodiazepine Receptor". Journal of Medicinal Chemistry 20040325 US, Mar. 25, 2004, vol. 47, No. 7, pp. 1852-1855.

Zhang et al; "Modulation of Peripheral-Type Benzodiazepine Receptor During Ishemia Reperfusion Injury in a Pig Kidney Model: A New Partner of Leukemia Inhibitory Factor in Tubular Regeneration". J Am Coll Surg; 203 (3), 2006, pp. 353-364.

Hammound et al; "Imaging Glial Cell Activation With [11C]-R-PK11195 in Patients With AIDS". 2005, J of Neurovirology 11, pp. 346-355.

Tam et al; "Development of Scarring and Renal Failure in a Rat Model of Crescentic Glomerulonephritis". 1999, Nephrol Dial Transplant, 14 (7), pp. 1658-1666.

Cook et al; "Interleukin-4 Ameliorates Crescentic Glomerulonephritis in Wistar Kyoto Rats" 1999, Kidney Int; 55 (4) pp. 1319-1326.

* cited by examiner

ACTIVE ENANTIOMER

CROSS-REFERENCE TO RELATED APPLICATIONS

This continuation-in-part application claims benefit of priority to Indian patent application no. 1824/DEL/2010, filed Aug. 2, 2010, and to International Application No. PCT/EP2010/053998, filed Mar. 26, 2010, which in turn claims benefit of priority to U.S. Provisional Application No. 61/164,131, filed Mar. 27, 2009, the entire disclosure of each which is hereby incorporated by reference.

TECHNICAL FIELD OF THE INVENTION

The present invention concerns in vivo imaging and in particular positron-emission tomography (PET) imaging of peripheral benzodiazepine receptors (PBR). An indole-based PET tracer is provided that binds with high affinity to PBR, has good uptake into the brain following administration, and which has excellent selective binding to PBR. The present invention also provides a precursor compound useful in the synthesis of the PET tracer of the invention, as well as a method for synthesis of said precursor compound. Other aspects of the invention include a method for the synthesis of the PET tracer of the invention comprising use of the precursor compound of the invention, a kit for carrying out said method, and a cassette for carrying out an automated version of said method. In addition, the invention provides a radiopharmaceutical composition comprising the PET tracer of the invention, as well as methods for the use of said PET tracer.

Description of Related Art

Peripheral benzodiazepine receptors (PBR) are known to be mainly localised in peripheral tissues and glial cells but their physiological function remains to be clearly elucidated. PBR are also referred to as translocator proteins (TSPO). Subcellularly, PBR are known to localise on the outer mitochondrial membrane, indicating a potential role in the modulation of mitochondrial function and in the immune system. It has furthermore been postulated that PBR are involved in cell proliferation, steroidogenesis, calcium flow and cellular respiration.

Abnormal PBR expression has been associated with inflammatory disease states of the central nervous system (CNS), including multiple sclerosis (Banati et al 2001 Neuroreport; 12(16): 3439-42; Debruyne et al 2002 Acta Neurol Bag; 102(3): 127-35), Rasmeussen's encephalitis (Banati et al 1999 Neurology; 53(9): 2199-203) cerebral vasculitis (Goerres et al 2001 Am J Roentgenol; 176(4): 1016-8), herpes encephalitis (Cagnin et al 2001 Brain; 124(Pt 10): 2014-27), and AIDS-associated dementia (Hammoud et al 2005 J Neurovirol; 11(4): 346-55).

Also in the CNS, a link with PBR has been documented in degenerative diseases such as Parkinson's disease (Gerhard et al 2006 Neurobiol Dis; 21(2): 404-12; Ouchi et al 2005 Ann Neurol; 57(2): 161-2), corticobasal degeneration (Gerhard et al 2004 Mov Disord; 19(10): 1221-6), progressive supranuclear palsy (Gerhard et al 2006 Neurobiol Dis; 21(2): 404-12), multiple system atrophy (Gerhard et al 2003 Neurology; 61(5): 686-9), Huntington's Disease (Pavese et al 2006 Neurology; 66(11): 1638-43; Tai et al 2007 Brain Res Bull; 72(2-3): 148-51), amyotrophic lateral sclerosis (Turner et al 2004 Neurobiol Dis; 15(3): 601-9), and Alzheimer's disease (Cagnin et al 2001 Lancet; 358(9283): 766; Yasuno et al 2008 Biol Psychiatry; 64(10): 835-41).

A number of CNS ischemic conditions have been shown to be related to abnormal expression of PBR, including; ischemic stroke (Gerhard et al 2005 Neuroimage; 24(2): 591-5), peripheral nerve injury (Banati et al 2001 Neuroreport; 12(16):3439-42), epilepsy (Sauvageau 2002 Metab Brain Dis; 17(1): 3-11; Kumar et al 2008 Pediatr Neural; 38(6)). PBR have been postulated as a biomarker to determine the extent of damage in traumatic brain injury (Toyama et al 2008 Ann Nucl Med; 22(5): 417-24), with an increase in expression of PBR reported in an animal model of traumatic brain injury (Venneti et al 2007 Exp Neural; 207(1): 118-27). Interestingly, acute stress has been correlated with an increase in expression of PBR in the brain, whereas chronic stress has been correlated with a downregulation of PBR (Lehmann et al 1999 Brain Res; 851(1-2): 141-7). Delineation of glioma borders has been reported to be possible using [$^{11}$C]PK11195 to image PBR (Junck et al 1989 Ann Neurol; 26(6): 752-8). PBR may also be associated with neuropathic pain, Tsuda et al having observed activated microglia in subjects with neuropathic pain (2005 TINS 28(2) pp 101-7).

In the periphery, expression of PBR has been linked with lung inflammation (Branley et al 2008 Nucl. Med. Biol; 35(8): 901-9), chronic obstructive pulmonary disease and asthma (Jones et al 2003 Eur Respir J; 21(4): 567-73), inflammatory bowel disease (Ostuni et al Inflamm Bowel Dis; 2010 online publication), rheumatoid arthritis (van der Laken et al 2008 Arthritis Rheum; 58(11): 3350-5), primary fibromyalgia (Faggioli et al 2004 Rheumatology; 43(10): 1224-1225), nerve injury (Durrenberger et al 2004 J Peripher Nerv Syst; 9(1): 15-25), atherosclerosis (Fujimura et al 2008 Atherosclerosis; 201(1): 108-111), colon, prostate and breast cancer (Deane et al 2007 Mol Cancer Res; 5(4): 341-9; Miettinen et al 1995 Cancer Res; 55(12): 2691-5; Han et al 2003 J Recept Signal Transduct Res; 23(2-3): 225-38), kidney inflammation (Tam et al 1999 Nephrol Dial Transplant; 14(7): 1658-66; Cook et al 1999 Kidney Int; 55(4): 1319-26), and ischemia-reperfusion injury (Zhang et al 2006 J Am Coll Surg; 203(3): 353-64).

Positron emission tomography (PET) imaging using the PBR selective ligand, (R)-[$^{11}$C]PK11195 provides a generic indicator of central nervous system (CNS) inflammation. However, (R)-[$^{11}$C]PK11195 is known to have high protein binding, and low specific to non-specific binding. Furthermore, the role of its radiolabelled metabolites is not known, and quantification of binding requires complex modelling. Consequently, there have been efforts to develop an in vivo imaging agent for PBR that does not suffer from these problems. One such in vivo imaging agent is the tricyclic indole derivative described in co-pending patent application PCT/EP2010/053998. The tricyclic indole derivative described in PCT/EP2010/053998 has good affinity for PBR, has excellent brain uptake and specificity for PBR, and a high proportion of radioactivity in the brain at 60 minutes post-injection represents the parent in vivo imaging agent. PCT/EP2010/053998 discloses that an especially preferred in vivo imaging agent is the following $^{18}$F-labelled compound:

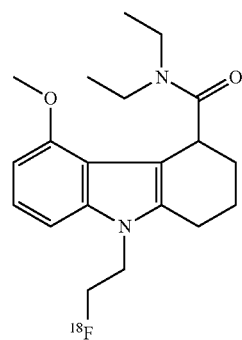

There is scope for an even further improved in vivo imaging agent for imaging PBR.

SUMMARY OF THE INVENTION

Figure 1:
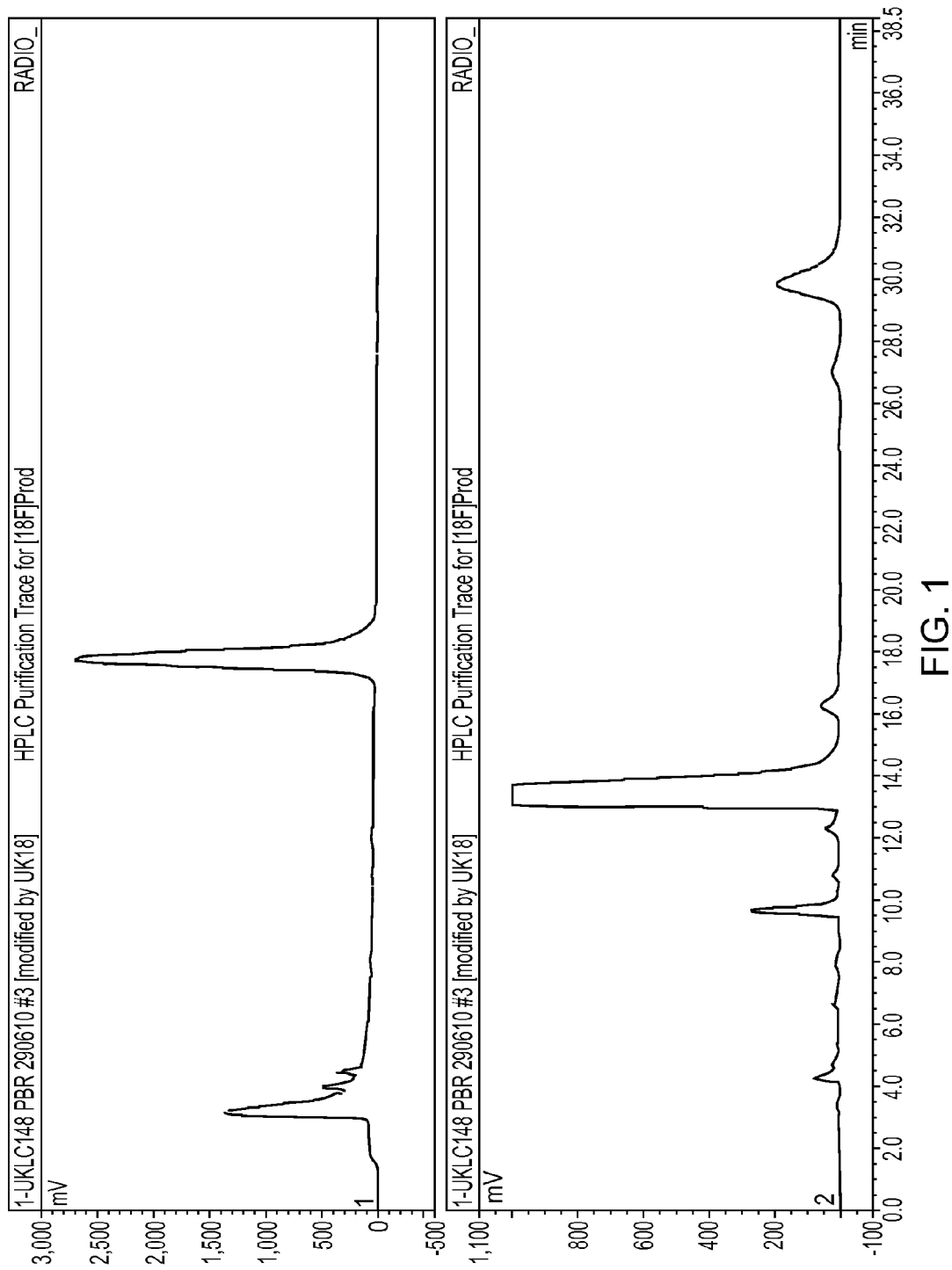
FIGS. 1 and 4 show radioactive (top) and UV (bottom) HPLC traces obtained using a semi-preparative method for the PET tracer of the invention and its alternative enantiomer, respectively.

The present invention provides a PET tracer that retains the advantageous properties of the known tricyclic indole PET tracer, and also has a number of improved properties. It has been demonstrated that, in comparison to a known tricyclic PET tracer, the PET tracer of the invention has improved binding affinity for PBR, marginally improved metabolism profile with a high proportion of activity at 60 minutes post-injection representing activity in the brain, and significantly improved specific binding to PBR-expressing tissues. The present invention also provides a precursor compound useful in the preparation of the PET tracer of the invention, as well as methods for the preparation of said precursor compound and said PET tracer. Also provided by the present invention is a radiopharmaceutical composition comprising the PET tracer of the invention. Methods for using the PET tracer and the radiopharmaceutical composition are also provided.

DETAILED DESCRIPTION OF THE INVENTION

PET Tracer

In one aspect, the present invention provides a positron-emission tomography (PET) tracer having the following chemical structure:

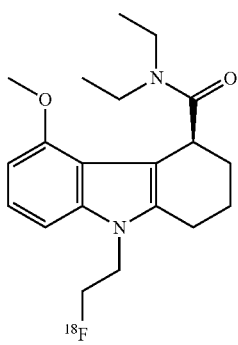 [SMILES: CCN(CC)C(=O)[C@H]1CCCc2c1c1c(OC)cccc1n2CC[18F]]

wherein the chiral centre has (S) configuration.

A "PET tracer" is a chemical compound that comprises a positron-emitting isotope, wherein the chemical compound is designed to target a particular physiology or pathophysiology in a biological system. The presence of the positron-emitting isotope allows the PET tracer to be detected following administration to the biological system and thereby facilitate detection of the particular physiology or pathophysiology.

The PET tracer of the invention has been shown to have an affinity almost 5 times greater than that of its alternative enantiomer, and nearly twice that of the racemic mixture. It has also been found that the PET tracer of the invention performs better in vivo as compared with its alternative enantiomer. The PET tracer of the invention also performs better in vivo as compared with the racemic mixture comprising said PET tracer and its alternative enantiomer.

The alternative enantiomer of the PET tracer of the invention has the following structure:

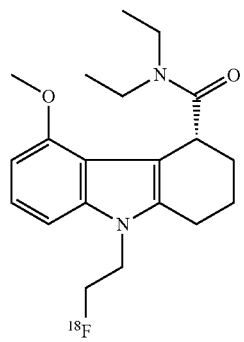 [SMILES: CCN(CC)C(=O)[C@@H]1CCCc2c1c1c(OC)cccc1n2CC[18F]]

wherein the chiral centre has (R) configuration.

The term "enantiomer" as used in the present invention refers to an enantiopure compound, i.e. one of the two mirror-image forms of an optically active molecule. An enantiomer is therefore a compound having only one chirality, wherein the term "chirality" refers to that property of a compound whereby it lacks an internal plane of symmetry and has a non-superimposable mirror image. The feature that is most often the cause of chirality in chemical compounds is the presence of an asymmetric carbon atom. An equimolar mixture of a pair of enantiomers is referred to herein as a "racemate" or as a "racemic mixture".

In the biodistribution experiment described in Example 9 it is shown that the PET tracer of the invention has improved binding to PBR-rich tissue in the brain (i.e. olfactory bulb) compared with both its alternative enantiomer and the racemic mixture. The results of the in vivo blocking experiment described in Example 11 confirm this finding. The results of the experiment described in Example 10 demonstrate that the activity in the brain at 60 minutes due to parent compound is improved for the PET tracer of the invention compared with the racemic mixture of the PET tracer and its alternative enantiomer. Furthermore, in the autoradiography experiment described in Example 12, it was demonstrated that the PET tracer of the invention had higher selective binding to areas of neuroinflammation as compared with the racemic mixture comprising said PET tracer and its alternative enantiomer. It was also found that the PET tracer of the invention does not racemise following incubation in human plasma or in rat $S_9$ fraction for extended periods, as described in Example 8 below.

Precursor Compound

The PET tracer of the invention may be prepared via a suitable precursor compound. Therefore, in another aspect, the present invention provides a precursor compound for the preparation of the PET tracer of the invention, wherein said precursor compound is of Formula I:

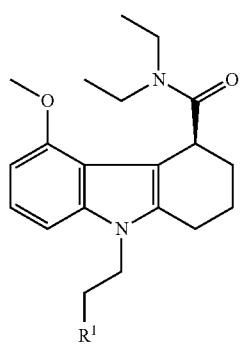

wherein R¹ is hydroxyl or is a leaving group selected from chloro, bromo, iodo, mesylate, tosylate, nosylate and triflate.

A "precursor compound" comprises a non-radioactive derivative of the PET tracer of the invention, designed so that chemical reaction with a convenient chemical form of $^{18}F$ occurs site-specifically; can be conducted in the minimum number of steps (ideally a single step); and without the need for significant purification (ideally no further purification), to give the PET tracer of the invention. Such precursor compounds are synthetic and can conveniently be obtained in good chemical purity.

A "leaving group" in the context of the present invention refers to an atom or group of atoms that is displaced as a stable species during a substitution or displacement radiofluorination reaction. Preferably, said leaving group is selected from mesylate, tosylate and triflate, and is most preferably mesylate. Where the leaving group is mesylate the precursor compound is referred to herein as "precursor compound 1".

Preparation of Precursor Compound

The precursor compound of the invention may be obtained by a variety of different routes, each of which forms a separate aspect of the present invention.

Accordingly, the present invention provides a first method to prepare the precursor compound of Formula I as defined herein, wherein said method comprises:

(i) providing a racemic mixture of said precursor compound of Formula I, as defined herein, and a compound of Formula II:

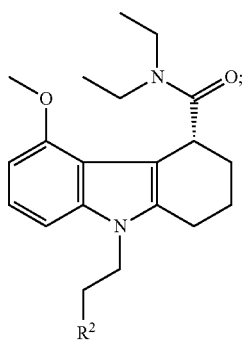

wherein R² is as defined above for R¹, and R¹ and R² are the same;

(ii) separating said precursor compound of Formula I from said compound of Formula II.

The step of "separating" said precursor compound of Formula I from said compound of Formula II is carried out by an enantiomeric separation technique. Suitable enantiomeric separation techniques include high performance liquid chromatography (HPLC), supercritical fluid chromatography (SFC), simulated bed chromatography (SBC). A detailed assessment of the various techniques that may be applied for enantiomeric separation can be found in "Chiral Separation Techniques: a Practical Approach" (2007 Wiley; Subramanian, Ed.).

Scheme 1 below illustrates one method to obtain a racemic mixture of the precursor compound of Formula I and the compound of Formula II:

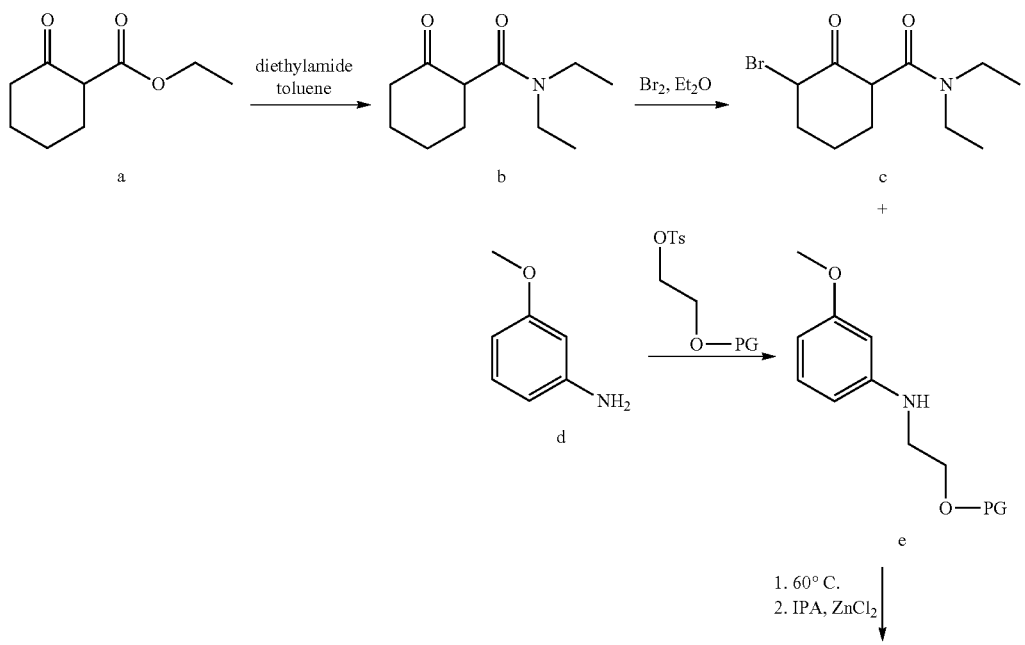

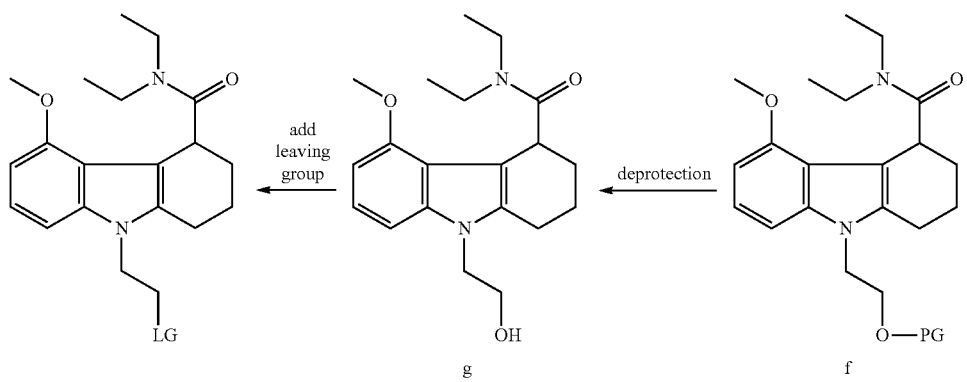

In Scheme 1, PG represents a hydroxyl protecting group; LG represents a leaving group as defined herein; OTs represents the leaving group tosylate; and, IPA represents isopropyl alcohol. Compound g is a precursor compound of the invention where $R^1$ is hydroxyl. Suitable hydroxyl protecting groups are well-known in the art and include acetyl, benzyl, benzoyl, silyl ethers, alkyl ethers, and alkoxymethyl ethers. Protecting groups are discussed in more detail by Theorodora W. Greene and Peter G. M. Wuts in "Protective Groups in Organic Synthesis" (Fourth Edition, John Wiley & Sons, 2007). In the context of the present invention a preferred hydroxyl protecting group is benzyl. Scheme 1 above is based on the methods to obtain similar compounds described by Napper et al (J Med Chem 2005; 48: 8045-54) and by Davies et al (J Med Chem 1998; 41: 451-467).

An alternative method to obtain a racemic mixture of the precursor compound of Formula I and the compound of Formula II is illustrated in Scheme 2 below:

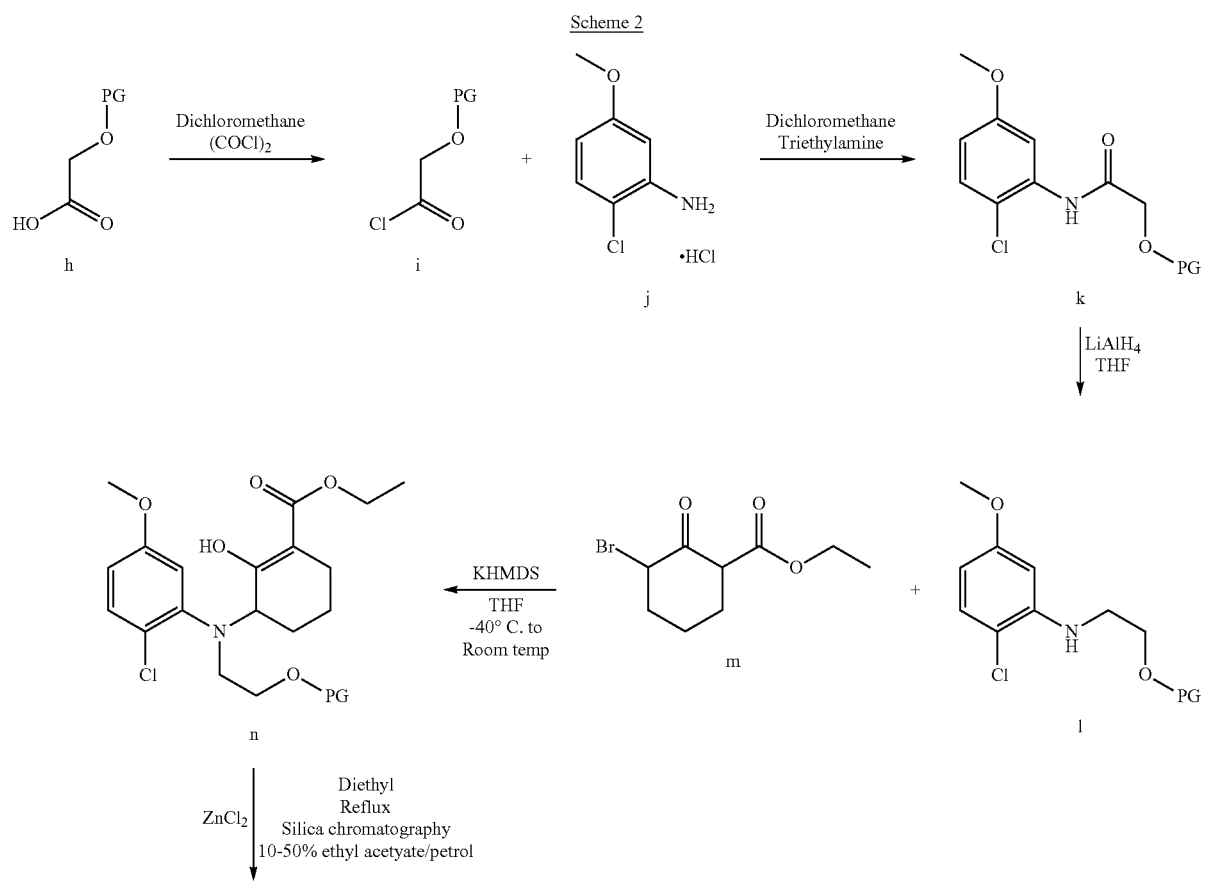

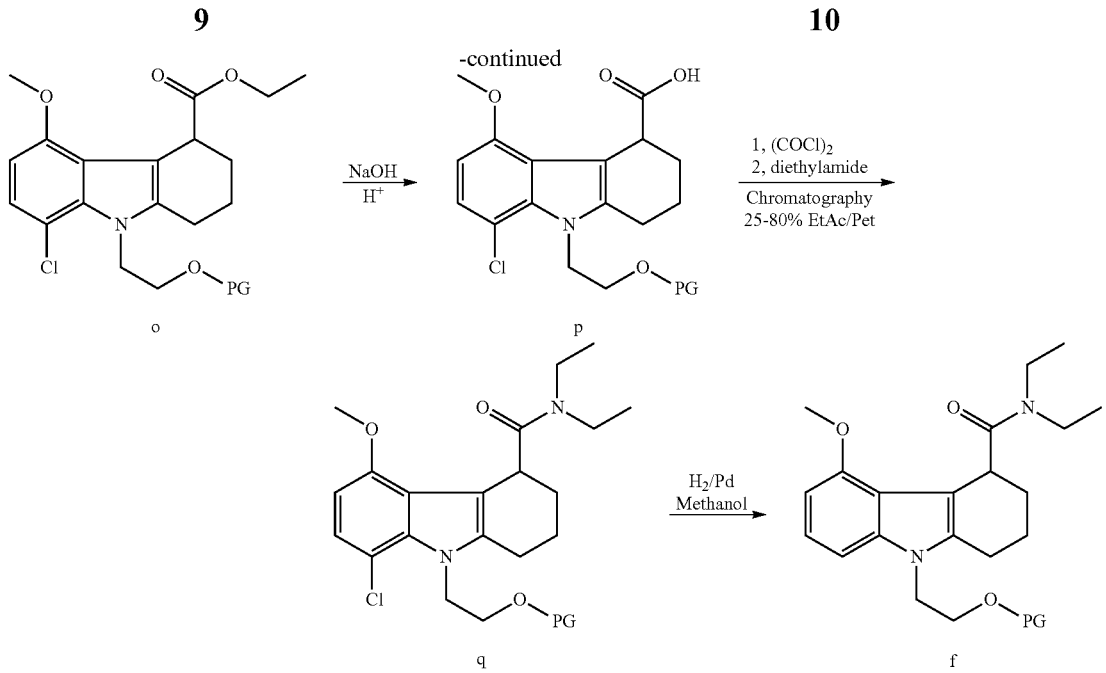

In Scheme 2 PG is a hydroxyl protecting group as defined above, THF is tetrahydrofuran, KHMDS is potassium bis(trimethylsilyl)amide. From compound f, Scheme 2 continues as illustrated in Scheme 1 from compound f to obtain the resultant racemic mixture. Scheme 2 is based on the method disclosed in WO 2003/014082. In this synthetic route, the chlorine at the bottom position on the left-had side ring forces the cyclisation to take place in just one way. However, when the present inventors directly applied the teachings of WO 2003/014082 to obtain the racemic mixture of the precursor compound of Formula I and the compound of Formula II, the yield was low. This problem was overcome by changing the solvent system used for the cyclisation step. In WO 2003/014082 the cyclisation step is carried out in toluene, whereas the present inventors found that optimum yields were obtained when diethyl ether was used in place of toluene. The product of the cyclisation step dissolves in diethyl ether whereas the uncyclised starting compound does not. The uncyclised starting compound therefore remains with the $ZnCl_2$ at the bottom of the reaction vessel, and the cyclised product moves into the diethyl ether at the top of the reaction vessel.

A second method to obtain the precursor compound of Formula I comprises:
(i) providing a compound of Formula III:

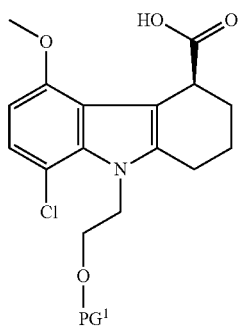

(III)

wherein $PG^1$ is a hydroxyl protecting group;

(ii) converting said compound of Formula III to its corresponding acid chloride;
(iii) reacting the acid chloride obtained in step (ii) with diethylamide to obtain a compound of Formula IV:

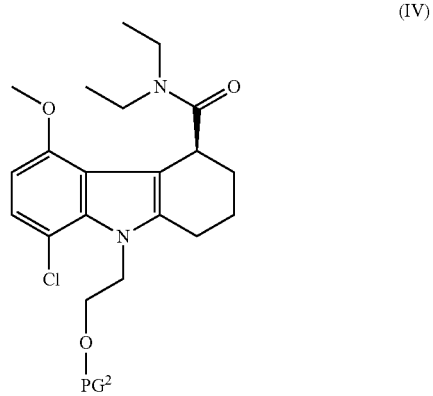

(IV)

wherein $PG^2$ is a hydroxyl protecting group and is the same as $PG^1$;
(iv) deprotecting the compound of Formula IV obtained in step (iii) to obtain the hydroxyl derivative;
(v) adding a leaving group as defined herein.

Both steps (iv) and (v) result in a precursor compound of Formula I as defined herein.

Step (ii) of "converting" said compound of Formula III to the acid chloride may be carried out with a reagent selected from oxalyl chloride, thionyl chloride, phosphorus trichloride, or phosphorus pentachloride. Oxalyl chloride is preferred.

The step of "deprotecting" refers to the removal of the hydroxyl protecting group, and may be carried out by means well-known to those skilled in the art. The hydroxyl protecting group $PG^1$ is as defined above for PG in Scheme 1. The method used is tailored to the particular hydroxyl protecting group. Typical strategies for removal of hydroxyl protecting groups include hydrogenolysis, and treatment with an acid or with a base.

The step of "adding" the leaving group may carried out by reacting compound g of Scheme 1 above with a halide derivative of the desired leaving group under suitable reaction conditions. For example, to add a mesylate, compound g in Scheme 1 above may be reacted with methanesulfonyl chloride in the presence of a base, for example an amine base such as triethylamine.

In step (i) of said second method to obtain the precursor compound of Formula I, the compound of Formula III can be provided by various routes. For example, by means of a method comprising:

(a) providing an equimolar mixture of a compound of Formula V and a compound of Formula VI:

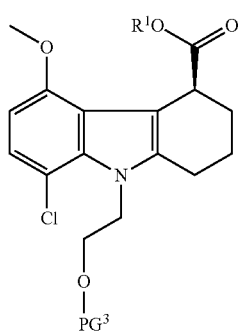

(V)

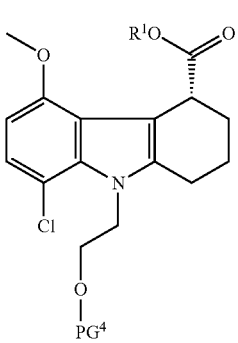

(VI)

wherein:
R$^1$ is a chiral alcohol; and,
PG$^3$ and PG$^4$ are the same and are each a hydroxyl protecting group;

(b) separating the compound of Formula V from the compound of Formula VI;

(c) removing R$^1$ from the separated compound of Formula V using acidic conditions thereby resulting in said compound of Formula III.

The term "chiral alcohol" refers to an enantiomer of an optically-active alcohol, wherein the term "enantiomer" is as previously defined herein. The term "alcohol" refers to an organic compound that comprises a hydroxyl group attached to a carbon atom. Preferred chiral alcohols for use in the above-described method are menthol and borneol.

The chiral alcohol is cleaved from the separated compound of Formula V by acid hydrolysis. Suitable acids for use in this step include hydrochloric acid or sulphuric acid, preferably 2 molar hydrochloric acid or 1 molar sulphuric acid.

In an alternative aspect, the compound of Formula III can be provided using a method comprising:

(a) providing a racemic mixture of said compound of Formula III and a compound of Formula VIII:

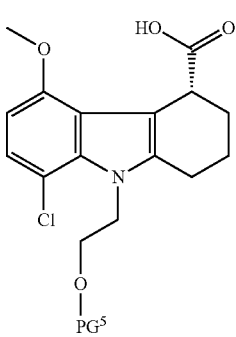

(VIII)

wherein PG$^5$ is a hydroxyl protecting group and is the same as PG$^1$ as defined above for Formula III;

(b) reacting the mixture as defined in step (a) with an optically active amine to separate said compound of Formula III from said compound of Formula VIII.

A racemic mixture of said compound of Formula III and said compound of Formula VIII can be obtained according to the method illustrated in Scheme 2 above, wherein the desired racemic mixture is compound p as illustrated therein.

A suitable optically active amine for use in the above-described method may be selected from S-Alpha-Methyl-Benzylamine, R-(+)-N-(1-Naphthylmethyl)-Alpha-Benzylamine, N-(2-Hydroxy) ethyl-Alpha-methyl benzyl amine, and 1(P-Tolyl) Ethylamine. Other optically active amines suitable for use in the above process are readily available commercially, e.g. from Aldrich chemical company.

Step (b) of reacting the mixture of step (a) with an optically active amine to separate said compound of Formula III from said compound of Formula IV initially generates two diasterisomeric salts. These diasterisomeric salts are separated by crystallization from a suitable solvent such as acetone, or ethyl acetate. The separated salts are treated with mineral acid such as 2N hydrochloric acid or 1M sulphuric acid to regenerate said compound of Formula III separated from said enantiomer of Formula VIII. The compound of Formula III is then recovered by extraction into ethyl acetate, separated from the aqueous layer and concentrated in vacuum to give the enantiomer of Formula III.

In a yet further alternative, the compound of Formula III can be obtained using a method comprising:

(a) providing a racemic mixture of a compound of Formula IX and a compound of Formula X:

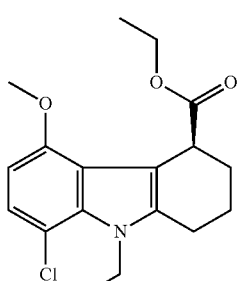

(IX)

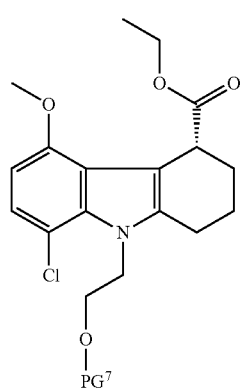

(X)

wherein PG$^6$ and PG$^7$ are the same and are each a hydroxyl protecting group;

(b) reacting the mixture as defined in step (a) with a stereo selective enzyme to obtain said compound of Formula III wherein said stereo selective enzyme effects ester hydrolysis of the compound of Formula IX.

The racemic mixture of said compound of Formula IX and said compound of Formula X can be obtained according to the method illustrated above in Scheme 2, wherein desired racemic mixture is compound o as illustrated therein.

A suitable stereo selective enzyme for use in the above-described method may be selected from *Candida antarctica* lipase B, porcine liver esterase, porcine pancreatic lipase, or other known stereo selective enzymes that act in a similar manner.

Preparation of PET Tracer

In a further aspect, the present invention provides a method to prepare the PET tracer of the invention wherein said method comprises reaction of the precursor compound of Formula I with a suitable source of $^{18}$F. Reaction with $^{18}$F can be achieved by nucleophilic displacement of a leaving group present at the R$^1$ position of the precursor compound of Formula I. The precursor compound may be labelled in one step by reaction with a suitable source of [$^{18}$F]-fluoride ion ($^{18}$F$^-$), which is normally obtained as an aqueous solution from the nuclear reaction $^{18}$O(p,n)$^{18}$F and is made reactive by the addition of a cationic counterion and the subsequent removal of water. Suitable cationic counterions should possess sufficient solubility within the anhydrous reaction solvent to maintain the solubility of $^{18}$F$^-$. Therefore, counterions that have been used include large but soft metal ions such as rubidium or caesium, potassium complexed with a cryptand such as Kryptofix™, or tetraalkylammonium salts. A preferred counterion is potassium complexed with a cryptand such as Kryptofix™ because of its good solubility in anhydrous solvents and enhanced $^{18}$F$^-$ reactivity. $^{18}$F can also be introduced by O-alkylation of a hydroxyl group at the R$^1$ position in the precursor compound with $^{18}$F(CH$_2$)$_3$-LG wherein LG represents a leaving group as defined above.

A more detailed discussion of well-known $^{18}$F labelling techniques can be found in Chapter 6 of the "Handbook of Radiopharmaceuticals" (2003; John Wiley and Sons: M. J. Welch and C. S. Redvanly, Eds.).

In a preferred embodiment, the method to prepare the PET tracer of the invention is automated. [$^{18}$F]-radiotracers may be conveniently prepared in an automated fashion by means of an automated radiosynthesis apparatus. There are several commercially-available examples of such apparatus, including Tracerlab™ and Fastlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The present invention therefore provides in another aspect a cassette for the automated synthesis of the PET tracer as defined herein comprising:
  i) a vessel containing the precursor compound of Formula I as defined herein; and,
  ii) means for eluting the vessel of step (i) with a suitable source of $^{18}$F as defined herein.

For the cassette of the invention, the suitable and preferred embodiments of the precursor compound of Formula I, and of the suitable source of $^{18}$F, are as previously defined herein.

The cassette may additionally comprise:
  iii) an ion-exchange cartridge for removal of excess $^{18}$F.

Radiopharmaceutical Composition

In a yet further aspect, the present invention provides a radiopharmaceutical composition comprising the PET tracer as defined herein together with a biocompatible carrier suitable for mammalian administration.

The "biocompatible carrier" is a fluid, especially a liquid, in which the PET tracer of the invention is suspended or dissolved, such that the radiopharmaceutical composition is physiologically tolerable, e.g. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

The radiopharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). Where the PET tracer of the invention is provided as a radiopharmaceutical composition, the method for preparation of said PET tracer may further comprise the steps required to obtain a radiopharmaceutical composition, e.g. removal of organic solvent, addition of a biocompatible buffer and any optional further ingredients. For parenteral administration, steps to ensure that the radiopharmaceutical composition is sterile and apyrogenic also need to be taken. Such steps are well-known to those of skill in the art.

PET Imaging Method

The PET tracer of the invention is useful for the in vivo detection of PBR receptor expression in a subject. Therefore in another aspect, the present invention provides a PET imaging method to determine the distribution and/or the extent of PBR expression in a subject, wherein said method comprises:
  i) administering to said subject the PET tracer as defined herein;
  ii) allowing said PET tracer to bind to PBR in said subject;
  iii) detecting signals emitted by the $^{18}$F comprised in said bound PET tracer;
  iv) generating an image representative of the location and/or amount of said signals; and,
  v) determining the distribution and extent of PBR expression in said subject wherein said expression is directly correlated with said signals.

The step of "administering" the PET tracer is preferably carried out parenterally, and most preferably intravenously. The intravenous route represents the most efficient way to deliver the PET tracer throughout the body of the subject, and therefore also across the blood-brain barrier (BBB) and into contact with PBR expressed in the central nervous system (CNS) of said subject. Intravenous administration neither represents a substantial physical intervention nor a substantial health risk to the subject. The PET tracer of the invention is preferably administered as the radiopharmaceutical composition of the invention, as defined herein. The administration step is not required for a complete definition of the PET imaging method of the invention. As such, the PET imaging method of the invention can also be understood as comprising the above-defined steps (ii)-(v) carried out on a subject to whom the PET tracer of the invention has been pre-administered.

Following the administering step and preceding the detecting step, the PET tracer is allowed to bind to PBR. For example, when the subject is an intact mammal, the PET tracer will dynamically move through the mammal's body, coming into contact with various tissues therein. Once the PET tracer comes into contact with PBR, a specific interaction takes place such that clearance of the PET tracer from tissue with PBR takes longer than from tissue without, or with less PBR. A certain point in time will be reached when detection of PET tracer specifically bound to PBR is enabled as a result of the ratio between PET tracer bound to tissue with PBR versus that bound in tissue without, or with less PBR.

The "detecting" step of the method of the invention involves detection of signals emitted by the $^{18}$F comprised in the PET tracer by means of a detector sensitive to said signals, i.e. a PET camera. This detection step can also be understood as the acquisition of signal data.

The "generating" step of the method of the invention is carried out by a computer which applies a reconstruction algorithm to the acquired signal data to yield a dataset. This dataset is then manipulated to generate images showing the location and/or amount of signals emitted by the $^{18}$F. The signals emitted directly correlate with the expression of PBR such that the "determining" step can be made by evaluating the generated image.

The "subject" of the invention can be any human or animal subject. Preferably the subject of the invention is a mammal. Most preferably, said subject is an intact mammalian body in vivo. In an especially preferred embodiment, the subject of the invention is a human. The in vivo imaging method may be used to study PBR in healthy subjects, or in subjects known or suspected to have a pathological condition associated with abnormal expression of PBR (hereunder a "PBR condition"). Preferably, said method relates to the in vivo imaging of a subject known or suspected to have a PBR condition, and therefore has utility in a method for the diagnosis of said condition.

Examples of such PBR conditions where in vivo imaging would be of use include multiple sclerosis, Rasmeussen's encephalitis, cerebral vasculitis, herpes encephalitis, AIDS-associated dementia, Parkinson's disease, corticobasal degeneration, progressive supranuclear palsy, multiple system atrophy, Huntington's Disease, amyotrophic lateral sclerosis, Alzheimer's disease, ischemic stroke, peripheral nerve injury, epilepsy, traumatic brain injury, acute stress, chronic stress, neuropathic pain, lung inflammation, chronic obstructive pulmonary disease, asthma, inflammatory bowel disease, rheumatoid arthritis, primary fibromyalgia, nerve injury, atherosclerosis, kidney inflammation, ischemia-reperfusion injury, and cancer, in particular cancer of the colon, prostate or breast. The PET tracer of the invention is particularly suited to in vivo imaging of the CNS due to its good brain uptake.

In an alternative embodiment, the PET imaging method of the invention may be carried out repeatedly during the course of a treatment regimen for said subject, said regimen comprising administration of a drug to combat a PBR condition. For example, the PET imaging method of the invention can be carried out before, during and after treatment with a drug to combat a PBR condition. In this way, the effect of said treatment can be monitored over time. PET is particularly well-suited to this application as it has excellent sensitivity and resolution, so that even relatively small changes in a lesion can be observed over time, a particular advantage for treatment monitoring.

In a further aspect, the present invention provides a method for diagnosis of a condition in which PBR is upregulated wherein said method comprises the PET imaging method as defined above, together with a further step (vi) of attributing the distribution and extent of PBR expression to a particular clinical picture.

In another aspect, the present invention provides the PET tracer as defined herein for use in the above-defined method for diagnosis. The present invention also provides the PET tracer as defined herein for use in the manufacture of the radiopharmaceutical composition as defined herein for use in the method for diagnosis as defined herein.

The suitable and preferred aspects of any feature present in multiple aspects of the present invention are as defined for said features in the first aspect in which they are described herein. The invention is now illustrated by a series of non-limiting examples.

BRIEF DESCRIPTION OF THE EXAMPLES

Example 1 describes the synthesis of the racemate comprising a racemic mixture of the precursor compound of Formula I and the enantiomer of Formula II.

Example 2 describes the synthesis of the non-radioactive racemate comprising a racemic mixture of the non-radioactive analogue of the PET tracer of the invention along with its alternative enantiomer.

Example 3 describes the synthesis of precursor compound 1/for active enantiomer.

Example 4 describes the synthesis of imaging agent 1/active enantiomer.

Example 5 describes the synthesis of non-radioactive imaging agent 1/active enantiomer.

Example 6 describes the method used to determine absolute stereochemistry.

Example 7 describes an in vitro assay used to assess the binding of non-radioactive Racemate 1 and its two enantiomers.

Example 8 describes the method used to investigate chiral stability of the PET tracer of the invention in vitro.

Example 9 describes a method used to assess the in vivo biodistribution of the PET tracer of the invention, its alternative enantiomer, and the racemic mixture of the two.

Example 10 describes an experiment to evaluate metabolism of the PET tracer of the invention, and the racemic mixture comprising said PET tracer and its alternative enantiomer.

Example 11 describes an in vivo Mocking assay used to evaluate the PET tracer of the invention, and the racemic mixture comprising said PET tracer and its alternative enantiomer.

Example 12 describes an animal model of inflammation used to evaluate the PET tracer of the invention, and the racemic mixture comprising said PET tracer and its alternative enantiomer.

| | |
|---|---|
| AUFS | absorbance units full scale |
| aq | aqueous |
| DCM | dichloromethane |
| DFT | density functional theory |
| DMAP | 4-Dimethylaminopyridine |
| DMF | dimethylformamide |
| EDC | 1-Ethyl-3[3-dimethylaminopropyl]carbodiimide Hydrochloride |
| EOS | end of synthesis |
| EtOAc | ethyl acetate |
| FNA | facial nerve axotomy |
| IPA | isopropyl alcohol |
| IR | infra red |
| LC-MS | liquid chromatography-mass spectrometry |
| MeCN | acetonitrile |
| MeOH | methanol |
| NMR | nuclear magnetic resonance |
| OBn | benzyloxy |
| OMs | mesylate |
| OTs | tosylate |
| PET | positron emission tomography |
| QMA | quaternary methyl ammonium |
| RT | room temperature |
| SFC | supercritical fluid chromatography |
| SPE | solid phase extraction |
| TLC | thin layer chromatography |
| Tol | toluene |
| VCD | vibrational circular dichroism |

EXAMPLES

Example 1

Synthesis of a Racemic Mixture of the Mesylate Precursor Compound of the Invention ("Precursor Compound 1") and Its Alternative Enantiomer Example 1(a)

Benzyloxy Acetyl Chloride (1)

To benzyloxyacetic acid (10.0 g, 60.0 mmol, 8.6 mL) in dichloromethane (50 mL) was added oxalyl chloride (9.1 g, 72.0 mmol, 6.0 mL) and DMF (30.0 mg, 0.4 mmol, 32.0 µL) and stirred at RT for 3 h. There was initially a rapid evolution of gas as the reaction proceeded but evolution ceased as the reaction was complete. The dichloromethane solution was concentrated in vacuo to give a gum. This gum was treated with more oxalyl chloride (4.5 g, 35.7 mmol, 30.0 mg, 0.4 mL), dichloromethane (50 mL), and one drop of DMF. There was a rapid evolution of gas and the reaction was stirred for a further 2 h. The reaction was then concentrated in vacuo to afford 11.0 g (quantitative) of Benzyloxy acetyl chloride (1) as a gum. The structure was confirmed by $^{13}$C NMR (75 MHz, CDCl$_3$) $\delta_C$ 73.6, 74.8, 128.1, 128.4, 128.6, 130.0, and 171.9.

Example 1(b)

2-Benzyloxy-N-(2-chloro-5-metnhoxy-phenyl) acetamide (2)

Benzyloxy acetyl chloride (1) (11.0 g, 60.0 mmol) and 2-chloro-5-methoxyaniline hydrochloride (11.7 g, 60.2 mmol) in dichloromethane (100 mL) at 0° C., was stirred and triethylamine (13.0 g 126.0 mmol, 18.0 mL) added slowly over 15 min. The stirred reaction was allowed to warm to RT over 18 h. There was a heavy precipitation of triethylamine hydrochloride. The dichloromethane solution was washed with 10% aqueous potassium carbonate (50 mL), dried over magnesium sulfate and concentrated in vacuo to afford 18.9 g (quantitative) of 2-Benzyloxy-N-(2-chloro-5-methoxy-phenyl) acetamide (2) as a gum. The structure was confirmed by $^{13}$C NMR (75 MHz, CDCl$_3$): $\delta_C$ 55.6, 69.6, 73.6, 106.2, 111.1, 114.1, 127.7, 128.3, 128.6, 129.2, 134.6, 136.5, 158.9, and 167.7.

Example 1(c)

(2-Benzyloxy-ethyl)-(2-chloro-5-methoxuphenyl) amine (3)

2-Benzyloxy-N-(2-chloro-5-methoxy-phenyl) acetamide (2) (18.9 g, 62.0 mmol) in THF (100 mL) was stirred and lithium aluminuim hydride (4.9 g, 130.0 mmol) was added slowly over 15 min. There was a rapid evolution of hydrogen gas as the first of the lithium aluminium hydride was added. The reaction was then heated to reflux for 4 h and allowed to stand at RT over the weekend. The reaction was then quenched by the dropwise addition of water (50 mL) to the stirred solution. There was a violent evolution of hydrogen causing the reaction mixture to reflux. The reaction was then concentrated in vacuum to a slurry. Water (200 mL) and ethyl acetate (200 mL) were added and the mixture vigorously shaken. The reaction was then filtered through celite to remove the precipitated aluminium hydroxide and the ethyl acetate solution was separated, dried over magnesium sulfate and concentrated in vacuo to afford 18.4 g (quantitative) of (2-Benzyloxy-ethyl)-(2-chloro-5-methoxyphenyl) amine (3) as a gum. The structure was confirmed by $^{13}$C NMR (75 MHz, CDCl$_3$) $\delta_C$ 43.3, 55.3, 68.2, 73.0, 98.1, 101.8, 111.6, 127.6, 127.7, 128.4, 129.3, 137.9, 144.8, and 159.5.

Example 1(d)

3-Bromo-2-hydroxy-cyclohex-1-enecarboxylic acid ethyl ester (4)

Ethyl 2-oxocyclohexanecarboxylate (30 g, 176 mmol, 28 mL) was dissolved in diethyl ether (30 mL) and cooled to 0° C. under nitrogen. Bromine (28 g, 176 mmol, 9.0 mL) was added dropwise over 15 min and the reaction mixture was allowed to warm to RT over 90 min. The mixture was slowly poured into ice-cold saturated aqueous potassium carbonate (250 mL) and extracted with ethyl acetate (3×200 mL). The combined organic layers were dried over magnesium sulfate, filtered, concentrated in vacuo and dried on the vacuum line for 18 h to afford 41.4 g (94%) of 3-Bromo-2-hydroxy-1-enecarboxylic acid ethyl ester (4) as a yellow oil. The structure was confirmed by $^{13}$C NMR (75 MHz, CDCl$_3$): $\delta_C$ 14.1, 17.7, 21.8, 32.0, 60.0, 60.8, 99.7, 166.3, and 172.8.

Example 1(e)

3[(2-Benzyloxy-ethyl)-(2-chloro-5-methoxy-phenyl)-amino]-2-hydroxy-cyclohex-1-ene carboxylic acid ethyl ester (5)

(2-Benzyloxy-ethyl)-(2-chloro-5-methoxyphenyl) amine (3) (10.0 g, 34.2 mmol) was stirred in dry THF (100 mL) at −40° C. under nitrogen and potassium bis(trimethylsilyl) amide (143.0 mL of a 0.5 M solution in toluene, 72.0 mmol) was added over 30 min. 3-bromo-2-hydroxycyclohex-1-enecarboxylic acid ethyl ester (4) (8.5 g, 34.2 mmol) in dry THF (10 mL) was then added and allowed to warm to RT over a period of 1.5 h. Acetic acid (10.0 g, 166 mmol, 10.0 mL) was added and concentrated in vacuo to remove the THF. Ethyl acetate (200 mL) and 10% aqueous potassium carbonate (100 mL) was added and the mixture vigorously shaken. The ethyl acetate solution was separated, dried over magnesium sulfate and concentrated in vacuo to afford 16.5 g (quantitative) of 3[(2-Benzyloxy-ethyl)-(2-chloro-5-methoxy-phenyl)-amino]-2-hydroxy-cyclohex-1-ene carboxylic acid ethyl ester (5) as a gum which was used crude in the next step. HPLC (Gemini 150×4.6 mm, 50-95% methanol/water over 20 min) of crude reaction mixture, 18.9 min (38%), 19.2 min (25%), 23.1 min (28%).

One component of the reaction was isolated $^{13}$C NMR (75 MHz, CDCl$_3$) $\delta_C$ 14.3, 20.6, 21.8, 26.4, 38.6, 43.0, 55.8, 60.5, 68.7, 73.3, 93.4, 106.3, 108.2, 119.3, 121.5, 127.5, 127.6, 128.3, 135.7, 137.0, 137.9, 155.7, and 175.0.

Example 1(f)

9-(2-Benzyloxy-ethyl)-8-chloro-5-methoxy-2,3,4,9,-tetrahydro-1H-carbazole-4-carboxylic acid ethyl ester (6)

Zinc chloride (7.1 g, 52.0 mmol) was added to 3[(2-Benzyloxy-ethyl)-(2-chloro-5-methoxy-phenyl)-amino]-2-hydroxy-cyclohex-1-ene carboxylic acid ethyl ester (5) (8.0 g, 17.0 mmol) in dry diethyl ether (150 mL) under nitrogen and heated at reflux for 5.5 h. As the reaction was refluxed a thick brown dense oil formed in the reaction. The reaction was then cooled and the supernatant diethyl ether decanted off, ethyl acetate (100 mL) was added, washed with 2 N HCl (50 mL) and with 10% aqueous potassium carbonate (50 mL). The diethyl ether layer was separated, dried over magnesium sulfate and concentrated in vacuo to afford an oil (2.0 g). The crude material was purified by silica gel chromatography eluting with petrol (A): ethyl acetate (B) (10-40% (B), 340 g, 22 CV, 150 mL/min) to afford 1.8 g of 9-(2-Benzyloxy-ethyl)-8-chloro-5-methoxy-2,3,4,9,-tetrahydro-1H-carbazole-4-carboxylic acid ethyl ester (6). The thick dense brown layer was treated with ethyl acetate (100 mL) and 2 N HCl (50 mL). The ethyl acetate solution was separated, washed with 10% aqueous potassium carbonate (50 mL), dried over magnesium sulfate and concentrated in vacuo to give an oil (5.2 g). Diethyl ether (100 mL) and anhydrous zinc chloride (7.0 g) were added. The mixture was heated at reflux for a further 5 days. The ether layer was decanted off from the dark gum, was washed with 2 N HCl (50 mL), dried over magnesium sulfate and concentrated in vacuo to give a gum (2.8 g). This gum was purified by silica gel chromatography eluting with petrol (A): ethyl acetate (B) (5-35% (B), 340 g, 150 mL/min) to afford 2.1 g of 9-(2-Benzyloxy-ethyl)-8-chloro-5-methoxy-2,3,4,9,-tetrahydro-1H-carbazole-4-carboxylic acid ethyl ester (6). Total material obtained was 4.1 g (50%) of 9-(2-Benzyloxy-ethyl)-8-chloro-5-methoxy-2,3,4,9,-tetrahydro-1H-carbazole-4-carboxylic acid ethyl ester (6). The structure was confirmed by 13C NMR (75 MHz, CDCl$_3$): $\delta_C$ 14.4, 20.5, 22.3, 27.5, 40.2, 43.9, 55.0, 60.2, 70.7, 73.3, 100.2, 107.5, 108.4, 120.1, 122.8, 127.4, 127.5, 128.2, 132.0, 137.4, 138.1, 152.6, and 175.8.

Example 1(g)

9-(2-Benzyloxy-ethyl)-8-chloro-5-methoxy-2,3,4,9,-tetrahydro-1H-carbazole-4-carboxylic acid (7)

To 9-(2-Benzyloxy-ethyl)-8-chloro-5-methoxy-2,3,4,9,-tetrahydro-1H-carbazole-4-carboxylic acid ethyl ester (6) (2.0 g, 4.1 mmol) in ethanol (50 mL) was added sodium hydroxide (1.1 g, 27.1 mmol) and water (5 mL) and heated at 80° C. for 18 h. The ethanol was then removed by evaporation in vacuo and the residue partitioned between diethyl ether (50 mL) and water (50 mL). The diethyl ether layer was separated, dried over magnesium sulfate and concentrated in vacuo to give a gum (71.0 mg). The aqueous layer was acidified to pH 1 with 2N HCl (20 mL) and extracted with dichloromethane (2×100 mL). The dichloromethane layer was dried over magnesium sulfate and concentrated in vacuo to afford 1.6 g (87%) of 9-(2-Benzyloxy-ethyl)-8-chloro-5-methoxy-2,3,4,9,-tetrahydro-1H-carbazole-4-carboxylic acid (7) as a foam. The structure was confirmed by $^{13}$C NMR (75 MHz; CDCl$_3$): $\delta_C$ 20.2, 22.2, 27.1, 39.7, 44.0, 55.1, 70.7, 73.3, 100.6, 106.3, 108.9, 123.0, 127.4, 127.5, 128.3, 132.0, 138.0, and 152.0.

Example 1(h)

9-(2-Benzyloxy-ethyl)-8-chloro-5-methoxy-2,3,4,9,-tetrahydro-1H-carbazole-4-carbonyl chloride (8)

9-(2-Benzyloxy-ethyl)-8-chloro-5-methoxy-2,3,4,9,-tetrahydro-1H-carbazole-4-carboxylic acid (7) (1.5 g, 3.7 mmol) was dissolved in dichloromethane (50 mL) and oxalyl chloride (700 mg, 5.5 mmol, 470 μL) and DMF (1 drop) were added and the reaction stirred at 20° C. for 2 h. There was a moderate evolution of gas for about 30 min as the reaction proceeded. The reaction was then concentrated in vacuo to give 9-(2-Benzyloxy-ethyl)-8-chloro-5-methoxy-2,3,4,9,-tetrahydro-1H-carbazole-4-carbonyl chloride (8) as a gum which was used into the next step without purification. The structure was confirmed by $^{13}$C NMR (75 MHz; CDCl$_3$): $\delta_C$ 20.8, 22.1, 26.4, 44.2, 51.8, 55.1, 70.7, 73.3, 100.7, 106.0, 108.6, 119.5, 123.4, 127.3, 127.7, 128.3, 131.9, 138.0, 138.2, 152.0. and 176.3.

Example 1(i)

9-(2-Benxyloxy-ethyl)-8-chloro-5-methoxy-2,3,4,9-tetrahydro-1H-carbazole-4-carboxylic acid diethylamide (9)

9-(2-Benzyloxy-ethyl)-8-chloro-5-methoxy-2,3,4,9,-tetrahydro-1H-carbazole-4-carbonyl chloride (8) (1.6 g, 3.7 mmol) was then dissolved in dichloromethane (50 mL), cooled to 0° C., stirred and diethylamine (810 mg, 11.0 mmol, 1.1 mL) was added dropwise. The reaction was allowed to warm to room temperature over a period of 18 h. The reaction mixture was then washed with 10% aqueous potassium carbonate (50 mL), separated, dried over magnesium sulfate and concentrated in vacuo to a gum. The crude material was crystallized from diethyl ether to afford 1.2 g (71%) of 9-(2-Benxyloxy-ethyl)-8-chloro-5-methoxy-2,3,4,9-tetrahydro-1H-carbazole-4-carboxylic acid diethylamide (9) as a white crystalline solid. The structure was confirmed by $^{13}$C NMR (75 MHz; CDCl$_3$): $\delta_C$ 13.0, 14.5, 19.8, 22.2, 27.9, 36.4, 40.4, 41.9, 43.8, 55.0, 70.8, 73.3, 100.2, 108.5, 108.6, 119.9, 122.5, 127.4, 127.5, 128.3, 131.5, 137.8, 138.2, 152.4, and 174.5.

Example 1(j)

9-(2-Benzyloxy-ethyl)-5-methoxy-2,3,4,9-tetrahydro-1H-carbazole-4-carboxylic acid diethylamine (10)

9-(2-Benxyloxy-ethyl)-8-chloro-5-methoxy-2,3,4,9-tetrahydro-1H-carbazole-4-carboxylic acid diethylamide (9) (1.0 g, 2.1 mmol) in methanol (100 ml) was shaken with 10% palladium on charcoal (1.0 g), triethylamine (2.9 mg, 2.9 mmol, 4 µL under an atmosphere of hydrogen gas for 18 h at 55° C. The reaction was then filtered through a pad of celite and the filtrate concentrated in vacuo to give a gum (908 mg). The gum was then taken up in dichloromethane (100 ml) and washed with 5% aqueous potassium carbonate solution (50 ml). The dichloromethane solution was then separated, dried over magnesium sulfate and concentrated in vacuo to afford a gum. The gum was then crystallised from diethyl ether (50 ml) and the crystals collected by filtration to afford 523 mg (57%) of 9-(2-Benzyloxy-ethyl)-5-methoxy-2,3,4,9-tetrahydro-1H-carbazole-4-carboxylic acid diethylamine (10). The structure was confirmed by $^{13}$C NMR (75 MHz; CDCl$_3$): $\delta_C$ 13.1, 14.6, 20.1, 22.0, 28.1, 364 40.5, 42.0, 43.0, 54.7, 68.8, 73.3, 99.4, 102.4, 107.8, 116.4, 121.2, 127.6, 127.6, 128.3, 135.6, 137.8, 138.0 153.6, and 175.0.

Example 1(k)

9-(2-hydroxyethyl)-5-methoxy-2,3,4,9-tetrahydro-1H-carbazole-4-carboxylic acid diethylamine (11)

9-(2-Benzyloxy-ethyl)-5-methoxy-2,3,4,9-tetrahydro-1H-carbazole-4-carboxylic acid diethylamine (10) (1.0 g, 2.1 mmol) in methanol (50 ml) was shaken with 10% palladium on charcoal (300 mg), and hydrogen gas excess for 18 h at 55° C. The reaction was then filtered through a pad of celite and the filtrate concentrated in vacuo to give 578 mg (100%) 9-(2-hydroxyethyl)-5-methoxy-2,3,4,9-tetrahydro-1H-carbazole-4-carboxylic acid diethylamine (ii) as a foam. The structure was confirmed by $^{13}$C NMR (75 MHz; CDCl$_3$): $\delta_C$ 13.0, 14.4, 20.0, 22.0, 28.0, 36.4, 40.6, 42.0, 54.7, 60.6, 99.2, 102.6, 107.0, 116.7, 121.1, 136.1, 137.5, 138.0 153.5, and 175.7.

Example 1(l)

Methanesulphonic acid 2-(4-diethylcarbamyl-5-methoxy-1,2,3,4-tetrahydro-carbazol-9-yl) ethyl ester 9-(2-Hydroxyethyl)-5-methoxy-2,3,4,9-tetrahydro-1H-carbazole-4-carboxylic acid diethylamine (11) (478 mg, 1.4 mmol) in dichloromethane (30 ml) was cooled to 0° C. and methanesulfonyl chloride (477 mg, 4.2 mmol, 324 µL) and triethylamine (420 mg, 4.2 mmol, 578 µL) were added and allowed to warm to RT overnight. The reaction was washed with 5% aqueous potassium carbonate solution. The layers were separated. The combined organics were dried over magnesium sulfate and concentrated in vacuo to give a gum (696 mg). The crude material was purified by silica gel chromatography eluting with petrol (A): ethyl acetate (B) (75-100% B, 22 CV, 120 g, 85 mL/min) to afford Methanesulphonic acid 2-(4-diethylcarbamyl-5-methoxy-1,2,3,4-tetrahydro-carbazol-9-yl) ethyl ester as a gum that crystallised from diethyl ether to give 346 mg (59%) of a colourless solid. The structure was confirmed by $^{13}$C NMR (75 MHz; CDCl$_3$): $\delta_C$ 13.1, 14.5, 20.0, 21.9, 28.0, 36.3, 36.7, 40.3, 41.8, 41.9, 54.7, 68.1, 100.0, 102.0, 109.0, 116.4, 122.0 135.1, 137.3, 153.8, and 174.6.

Example 2

Synthesis of a Racemic Mixture of the Non-Radioactive PET Tracer of the Invention and Its Alternative Enantiomer Example 2(a)

Fluoroethyl Tosylate (12)

2-Fluoroethanol (640 mg, 10 mmol, 0.6 mL) was dissolved in pyridine (10 mL) under nitrogen. The solution was stirred at 0° C. and tosyl chloride (4.2 g, 21.8 mmol) added portionwise to the solution over a period of 30 min, keeping the temperature below 5° C. The reaction was stirred at 0° C. for 3 h. Ice was slowly added followed by water (20 mL). The reaction mixture was extracted into ethyl acetate and washed with water. Excess pyridine was removed by washing with 1 N HCl solution until the aqueous layer became acidic. Excess tosyl chloride was removed by washing with 1 M aqueous sodium carbonate. The organic layer was washed with brine, dried over magnesium sulfate and concentrated in vacuo to give 2.1 g (98%) of fluoroethyl tosylate (12) as a colourless oil. The structure was confirmed by $^{13}$C NMR (75 MHz, CDCl$_3$): $\delta_C$ 21.6 (CCH$_3$), 68.5 (d, J$_{CF}$=173 Hz, OCH$_2$CH$_2$F), 80.6 (d, J$_{CF}$=173 Hz, OCH$_2$CH$_2$F), 128.0, 129.9, 132.6, and 145.1.

Example 2(b)

2-chloro-5-methoxy-phenyl) (2-fluoroethyl) amine (13)

2-Chloro-5-methoxyaniline hydrochloride (5.0 g, 26.0 mmol) was dissolved in DMF (50 mL) and sodium hydride (2.3 g, 60% in oil, 57.0 mmol) was added. The reaction was stirred for 30 minutes at RT under nitrogen. Fluoroethyl tosylate (12) (6.7 g, 31.0 mmol) in DMF (5 mL) was added dropwise and the reaction was stirred at RT for 2 h. The reaction was then heated at 100° C. for 18 h. The reaction was allowed to cool and the solvent was removed under reduced pressure. The residue was dissolved in ethyl acetate (100 mL) and washed with water (2×100 mL). The organics were collected, dried over magnesium sulfate and concentrated in vacuo to give a brown oil which was purified by silica gel chromatography eluting with petrol (A): ethyl acetate (B) (5-30% (B), 330 g, 18.1 CV, 120 mL/min) to afford 1.3 g (25%) of 2-chloro-5-methoxy-phenyl) (2-fluoroethyl) amine (13) as a yellow oil. The structure was confirmed by $^{13}$C NMR (75 MHz; CDCl$_3$): $\delta_C$ 43.8 (d, J$_{CF}$=23 Hz), 55.3, 82.0 (d, J$_{CF}$=165 Hz), 98.1, 102.2, 111.6, 129.5, 144.1, and 159.5.

Example 2(c)

3-[(2-Chloro-5-methoxy-phenyl)-(2-fluoroethyl) amino]-2-hydroxy-cyclohexyl-1-enecarboxylic acid ethyl ester (14)

A solution of 2-chloro-5-methoxy-phenyl) (2-fluoroethyl) amine (13) (6.1 g, 30.0 mmol) in THF (170 mL) was cooled to −40° C. Potassium bis(trimethylsilyl)amide (126.0 mL of a 0.5 M solution in toluene, 63.0 mmol) was added dropwise and the reaction stirred for 30 min at −40° C.) 3-Bromo-2-hydroxy-cyclohex-1-enecarboxylic acid ethyl ester (4; prepared according to Example 1(d)) (7.4 g, 30.0 mmol) in THF (30 mL) was added dropwise at −40° C. The cooling bath was removed and the reaction was stirred at RT for 4 h. The reaction was quenched with brine (300 mL) and extracted into ethyl acetate (2×400 mL), dried over magnesium sulfate and concentrated in vacuo to give 12.0 g (quantitative) of 3-[(2-Chloro-5-methoxy-phenyl)-(2-fluoroethyl) amino]-2-hydroxy-cyclohexyl-1-enecarboxylic acid ethyl ester (14) as a brown oil which was used crude in the next step. The structure as a mixture of isomers was confirmed by $^1$H NMR (300 MHz, CDCl$_3$): $\delta_H$ 1.08 (0.8H, t, J=9 Hz, CO$_2$CH$_2$CH$_3$), 1.22-1.33 (2.2 H, m, CO$_2$CH$_2$CH$_3$), 1.40-2.60 (7H, m, $\overline{4}$-, 5-, and 6-CH$_2$, CHN), 3.20-4.50 ($\overline{10}$H, m, NCH$_2$CH$_2$F, NCH$_2$CH$_2$F, OCH$_3$, C$\overline{H}$CO$_2$CH$_2$CH$_3$), 6.50-6.70 ($\overline{1H}$, m, CHC(OC$\overline{H_3}$)C HC$\overline{H}$), 6.$\overline{95}$ (0.5$\overline{H}$, dd, J=3 and 6 Hz, CHC(OCH$_3$)CHCH), $\overline{7}$.08 (0.5H, d, J=3 Hz, CHC(OCH$_3$)CHCH), and 7.20-$\overline{7.30}$ (1H, m, CHC(OCH$_3$)CHCH).

Example 2(d)

8-chloro-9-(2-Fluoroethyl)-5-methoxy-2,3,4,9-tetrahydro-1H-carbazole-4-carboxylic acid ethyl ester (15)

Synthesis of 8-Chloro-9-(2-fluoro-ethyl)-5-methoxy-2,3, 4,9-tetrahydro-1H-carbazole-4-carboxylic acid ethyl ester (15) was initially attempted using the conditions described in WO 2003/014082. A solution of 2-chloro-5-methoxy-phenyl) (2-fluoroethyl) amine (13; prepared according to Example 2(b)) (600 mg, 3.8 mmol) in dry THF (20 mL) was cooled in an ice bath and treated with potassium bis(trimethyl silyl) amide (16 mL of a 0.5 M solution in toluene, 8.0 mmol). After 30 minutes 3-Bromo-2-hydroxy-cyclohex-1-enecarboxylic acid ethyl ester (4; prepared according to Example 1(d)) (1.04 g, 4.2 mmol) in THF (4 mL) was added and the reaction was allowed to warm to RT over 2 hours. The reaction was quenched with saturated ammonium chloride solution and extracted twice with ether. The extracts were washed with water, brine, dried and concentrated in vacuo. The crude material was purified by silica gel chromatrography eluting with petrol (A) and ethyl acetate (B) (2.5-50% B, 50 g, 25 CV, 40 mL/min). The main spot was a mixture of three compounds. This mixture was refluxed in toluene (20 mL) with dry zinc chloride (1.7 g, 12.6 mmol) overnight. The reaction was concentrated in vacuo and the residue was partitioned between 1N HCL (25 mL) and ethyl acetate (25 mL) and then extracted once more with ethyl acetate. The organic layers were washed with water and brine, dried and concentrated in vacuo to afford a brown oil. 1H NMR indicated that it was a mixture of several compounds. TLC on silica in a range of solvents could not separate this mixture into separate spots. Comparison of the $^1$H NMR of the mixture with an authentic sample indicated that the mixture contained an estimated 25% of 8-Chloro-9-(2-fluoro-ethyl)-5-methoxy-2,3,4,9-tetrahydro-1H-carbazole-4-carboxylic acid ethyl ester (15).

A modified method was then carried out. 3-[(2-Chloro-5-methoxy-phenyl)-(2-fluoroethyl) amino]-2-hydroxy-cyclohexyl-1-enecarboxylic acid ethyl ester (14) (12.2 g, 30.0 mmol) was dissolved in diethyl ether (250 mL) and zinc chloride (16.4 g, 120.0 mmol) was added. The reaction was heated at reflux for 16 h. Ethyl acetate (500 mL) was added to dissolve everything and was washed with 2N HCl (200 mL), water (200 mL), 10% aqueous potassium carbonate (200 mL), dried over magnesium sulfate and concentrated in vacuo. The crude material was purified by silica gel chromatography eluting with petrol (A): ethyl acetate (B) (5-20% B, 12 CV, 10 g, 100 mL/min) to afford 5.3 g (50% over 2 steps) of 8-chloro-9-(2-Fluoroethyl)-5-methoxy-2,3,4,9-tetrahydro-1H-carbazole-4-carboxylic acid ethyl ester (15) as a yellow solid. The structure was confirmed by $^{13}$C NMR (75 MHz, CDCl$_3$): $\delta_C$ 14.4, 20.4, 22.2, 27.4, 40.1, 44.2 (d, J$_{CF}$=23 Hz), 55.1, 60.2, 83.9 (d, J$_{CF}$=173 Hz), 100.6, 107.9, 108.2, 119.8, 123.1, 131.9, 137.2, 152.7, and 175.7.

Example 2(e)

9-(2-Fluoroethyl)-5-methoxy-2,3,4,9-tetrahydro-1H-carbazole-4-carboxylic acid ethyl ester (16)

8-chloro-9-(2-Fluoroethyl)-5-methoxy-2,3,4,9-tetrahydro-1H-carbazole-4-carboxylic acid ethyl ester (15) (5.3 g, 15.0 mmol) was dissolved in methanol (180 mL) and triethylamine (1.8 g, 18.0 mmol, 2.5 mL) and 10% Pd/C (2 g in methanol (20 mL)) were added. The mixture was placed on the Parr hydrogenator and shaken for 18 h under a hydrogen atmosphere. The reaction was filtered through a pad of celite, washed with methanol and the solvent was removed in vacuo. The residue was dissolved in ethyl acetate (300 mL) and washed with 10% aqueous potassium carbonate (200 mL), dried over magnesium sulfate and concentrated in vacuo to give 4.2 g (88%) of 9-(2-Fluoroethyl)-5-methoxy-2,3,4,9-tetrahydro-1H-carbazole-4-carboxylic acid ethyl ester (16) as a light brown solid. The structure was confirmed by $^{13}$C NMR (75 MHz, CDCl$_3$): $\delta_C$ 14.3, 20.6, 21.8, 27.6, 40.3, 43.3 (d, J$_{CF}$=23 Hz), 54.9, 60.1, 82.0 d, J$_{CF}$=165 Hz), 99.8, 102.1, 107.3, 117.2, 121.8, 134.9, 137.6, 153.8, and 176.0.

HPLC (Gemini 150×4.6 mm, 50-95% methanol/water over 20 min) 13.6 min (94%).

Example 2(f)

9-(2-Fluoroethyl)-5-methoxy-2,3,4,9-tetrahydro-1H-carbazole-4-carboxylic acid (17)

8-chloro-9-(2-Fluoroethyl)-5-methoxy-2,3,4,9-tetrahydro-1H-carbazole-4-carboxylic acid ethyl ester (16) (380 mg, 1.2 mmol) was dissolved in ethanol (4 mL). A solution of sodium hydroxide (580 mg, 14.5 mmol) dissolved in 6 mL of water, was added. The reaction mixture was heated to reflux overnight. The solvent was removed in vacuo and the crude mixture diluted with water, acidified with 2 N HCl until acidic, and washed with dichloromethane. The organics were combined and dried over magnesium sulfate and concentrated in vacuo to give 347 mg (quantitative) of 9-(2-Fluoroethyl)-5-methoxy-2,3,4,9-tetrahydro-1H-carbazole-4-carboxylic acid (17) as an off white solid which was used crude into the next step. The structure was confirmed by $^{13}$C NMR (75 MHz; CDCl$_3$): $\delta_C$ 20.4, 21.9, 27.2, 39.9, 43.3 (d, $J_{CF}$=23 Hz), 55.1, 81.9 (d, $J_{CF}$=173 Hz), 100.3, 102.8, 106.2, 117.1, 122.2, 135.6, 137.8, 153.3, and 180.8.

Example 2(g)

9-(2-Fluoroethyl)-5-methoxy-2,3,4,9-tetrahydro-1H-carbazole-4-carbonyl chloride (18)

A solution of 9-(2-Fluoroethyl)-5-methoxy-2,3,4,9-tetrahydro-1H-carbazole-4-carboxylic acid (17) (347 mg, 1.2 mmol) in dry dichloromethane (2 mL) was stirred under nitrogen. Oxalyl chloride (453 mg, 3.6 mmol, 300 µL) was added followed by a drop of DMF. The reaction mixture was stirred at RT under nitrogen for 2 h then evaporated in vacuo to give 371 mg (quantitative) of 9-(2-fluoroethyl)-5-methoxy-2,3,4,9-tetrahydro-1H-carbazole-4-carbonyl chloride as a gum which was used in the next step without purification. The structure was confirmed by $^{13}$C NMR (75 MHz, CDCl$_3$): $\delta_C$ 20.2, 21.7, 26.4, 43.3 (d, $J_{CF}$=23 Hz), 54.9, 80.5, 83.1, 100.2, 102.2, 105.8, 116.7, 122.4, 135.5, 137.4, 153.5, and 176.6.

Example 2(h)

9-(2-Fluoroethyl)-5-methoxy-2,3,4,9-tetrahydro-1H-carbazole-4-carboxylic acid diethyl amide 9-(2-fluoroethyl)-5-methoxy-2,3,4,9-tetrahydro-1H-carbazole-4-carbonyl chloride (18) (371 mg, 1.2 mmol) was dissolved in dichloromethane (2 mL) and cooled to 0° C. diethylamine (177 mg, 2.4 mmol, 250 µL) was then added and the reaction was stirred overnight at RT. The reaction was quenched with 10% aqueous potassium carbonate (2 mL). The dichloromethane layer was collected through a phase separator then concentrated in vacuo. The crude material was purified by silica gel chromatography eluting with petrol (A): ethyl acetate (B) (50-100% (B), 50 g, 35.2 CV, 40 mL/min) to afford a pale yellow solid. The solid was next triturated with a minimum amount of diethyl ether to afford 240 mg (58%) of 9-(2-Fluoroethyl)-5-methoxy-2,3,4,9-tetrahydro-1H-carbazole-4-carboxylic acid diethyl amide. The structure was confirmed by $^{13}$C NMR (75 MHz, CDCl$_3$): $\delta_C$ 13.0, 14.6, 19.9, 21.9, 28.0, 36.3, 40.5, 41.9, 43.1 (d, $J_{CF}$=23 Hz), 54.7, 82.0 (d, $J_{CF}$=173 Hz), 99.7, 102.1, 108.3, 117.0, 121.5, 135.3, 137.4, 153.3, and 174.8.

Example 3

Synthesis of Precursor Compound 1 and Its Alternative Enantiomer

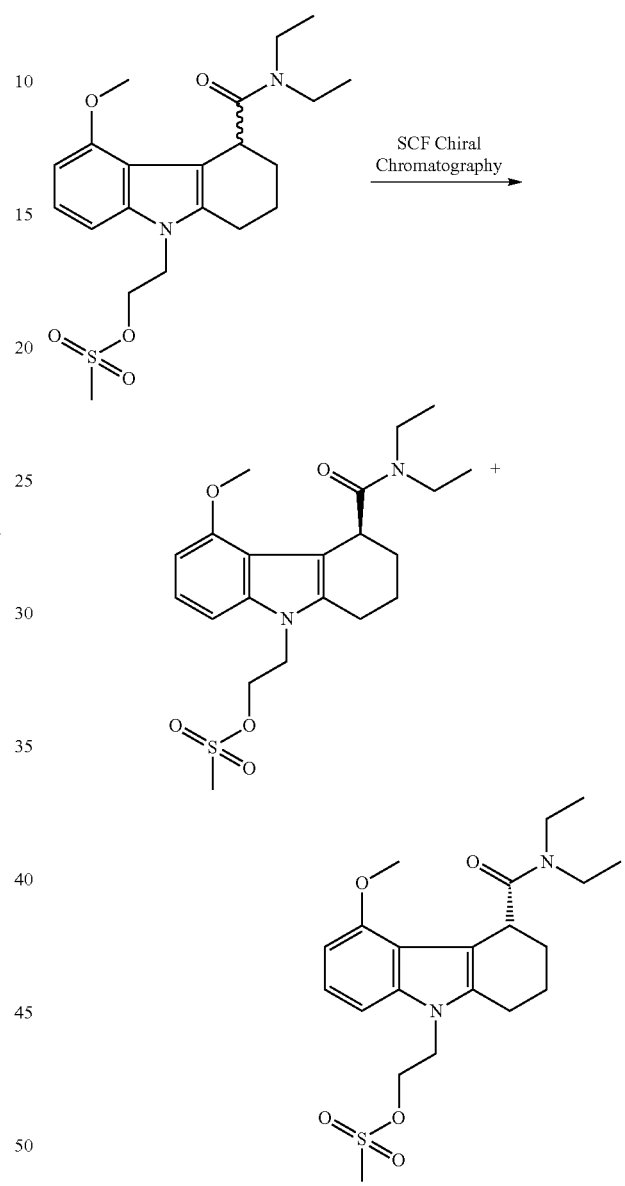

The racemic mixture of Precursor Compound 1 and its alternative enantiomer (obtained as described in Example 1) was separated into its enantiomers using chiral supercritical fluid (CO$_2$) chromatography on a Kromasil Amycoat, 250×10 mm, 5 µm, 100 Å column using 30% IPA at 40° C. at 13 ml a min with a run time of 6 min. 60 mg of the racemate was dissolved in 1.4-Dioxane (2 ml) and up to 200 µl at a time was as injected for each run. Baseline separation between the two enantiomers was achieved. Analytical HPLC determination of the enantiomeric purity of the two separated enantiomers on an IC from Chiral Technologies, 250×4.6 mm, 5 µm, run isocratic, 80:20—MeOH: IPA at 0.5 ml/min and room temperature indicated an enantiomeric purity of 99.5% of each of the enantiomers.

Example 4

Synthesis of the PET Tracer of the Invention and Its Alternative Enantiomer

Precursor compound 1 and its enantiomer obtained according to Example 3 were labelled with $^{18}$F using a FASTLab™ (GE Healthcare) cassette.

[$^{18}$F]Fluoride supplied from GE Healthcare on a GE PETrace cyclotron was trapped on a QMA cartridge. K222 (8 mg), KHCO$_3$ (200 µl, 0.1M aq.) and MeCN(1 ml) were added to eluant vial 1. 0.6 ml of eluant from eluant vial 1 was used to elute the QMA cartridge. Drying of the $^{18}$F eluate was carried out at 100° C. for 20 mins, followed by cooling to 86° C. before addition of precursor.

3 mg of each precursor compound was dissolved in 1.6 ml of CH$_3$CN. 1 ml of this solution was added to the reaction vessel. The reaction vessel was heated at 100° C. for 15 mins. The reaction vessel was then rinsed with 2 ml water.

Semi-preparative HPLC was carried out as follows:

| | |
|---|---|
| 0-40 mins | 45%(B) |
| Column | ACE 5 C18 column, 5u, 100 × 10 mm |
| Eluent | water (pump A): MeCN(pump B) |
| Loop Size | 5 ml |
| Pump speed | 3 ml/min, |
| Wavelength | 254 nm, 2 AUFS |

Figure 4:
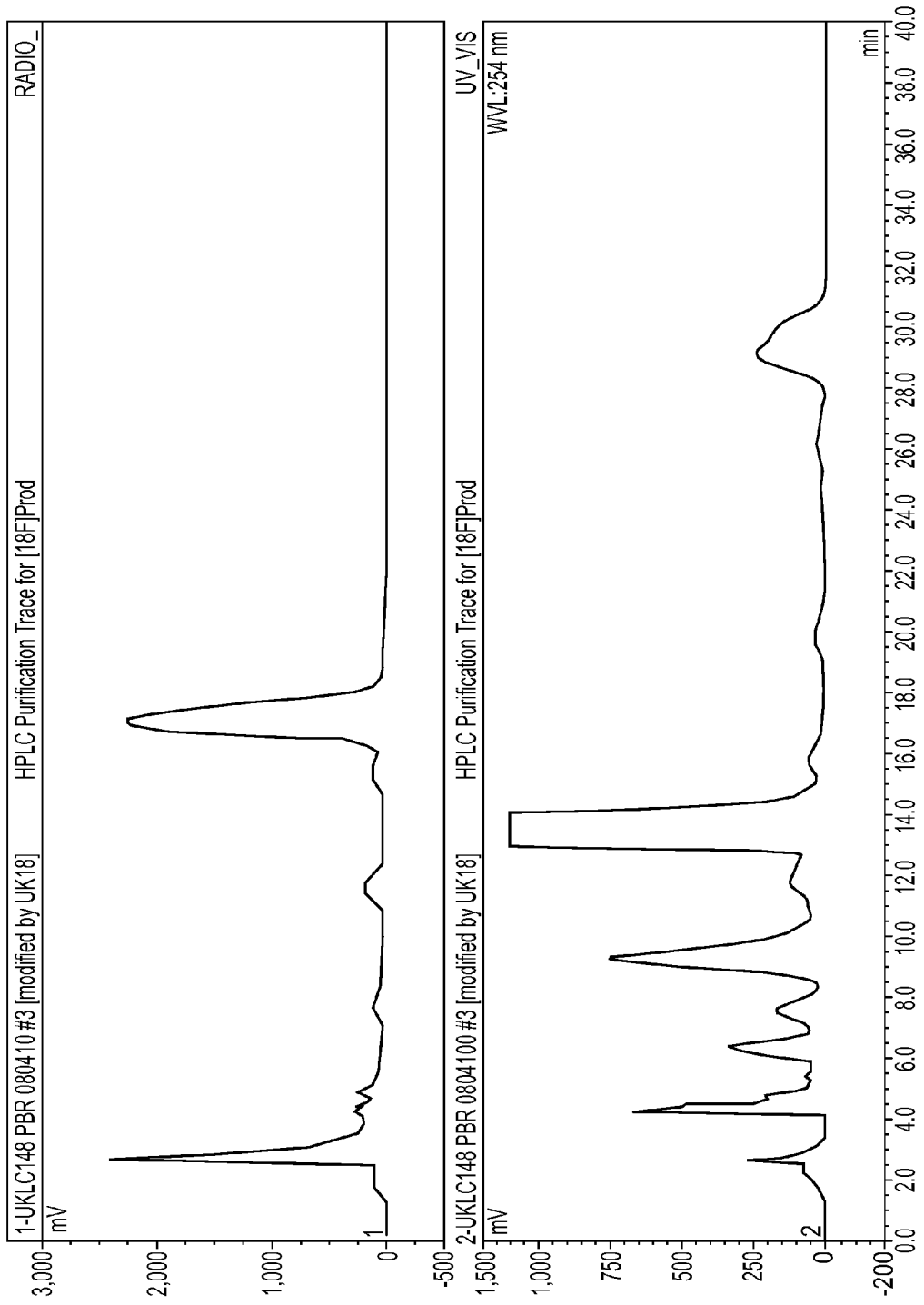

FIGS. 1 and 4 show the radioactive (top) and the UV (bottom) HPLC traces obtained using the above semi-preparative method for the PET tracer of the invention and its alternative enantiomer, respectively.

Analytical achiral HPLC was carried out as follows:

| | |
|---|---|
| 0-25 ins | 60%(B) |
| 25-25.5 mins | 60-95%(B) |
| 25.5-26.5 mins | 95%(B) |
| 26.5-27 mins | 95-60%(B) |
| 27-30 mins | 60%(B) |
| Column | Chromolith RP-18e 100 × 4.6 mm (H10-0022) Luna C18 Guard |
| Eluent | water (pump A): MeOH(pump B) |
| Loop Size | 20 ul |
| Pump speed | 1 ml/min, |
| Wavelength | 254, 230 nm |

Figure 2:
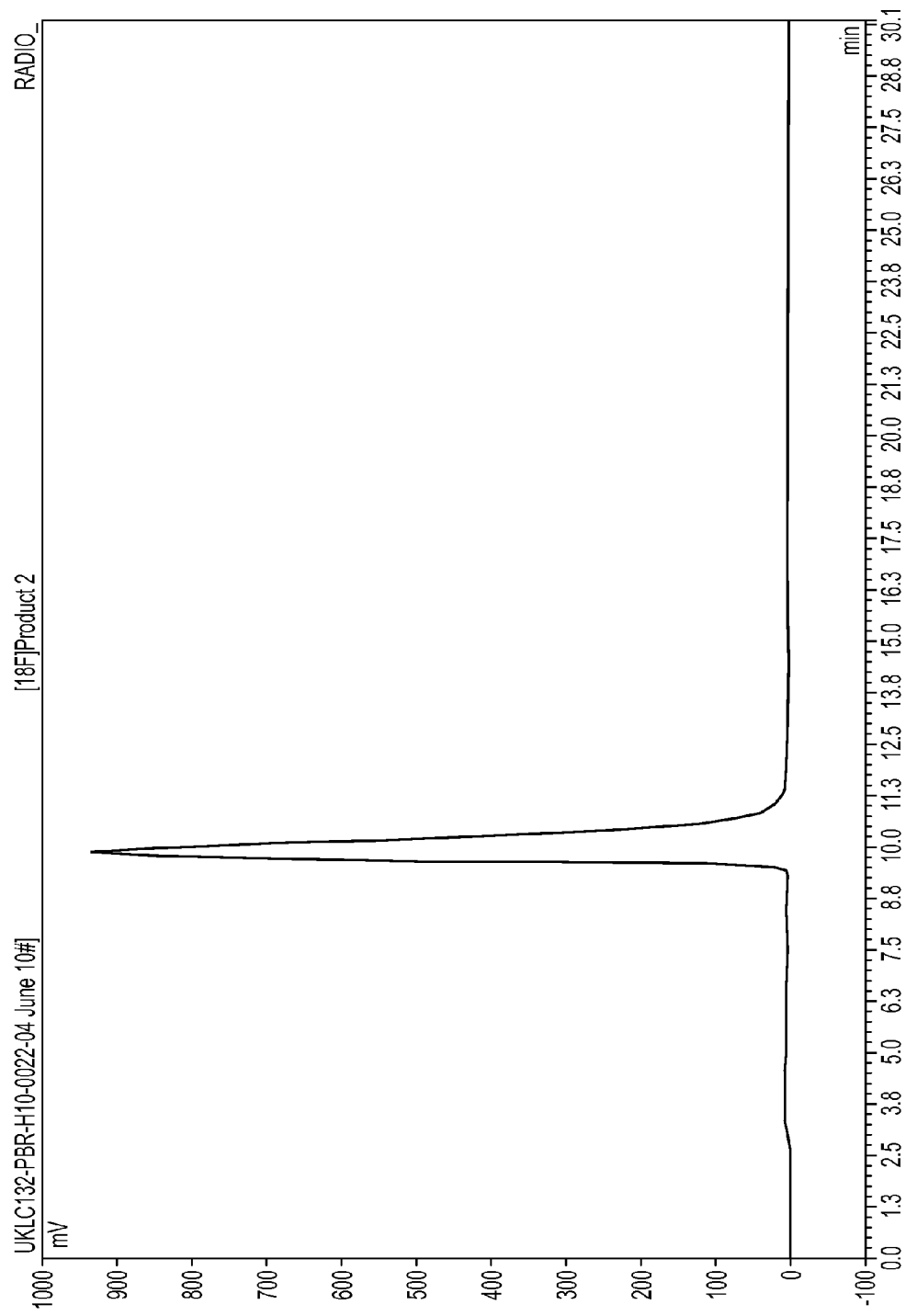
FIGS. 2 and 5 show HPLC traces obtained using an analytical achiral method for the PET tracer of the invention and its alternative enantiomer, respectively.
Figure 5:
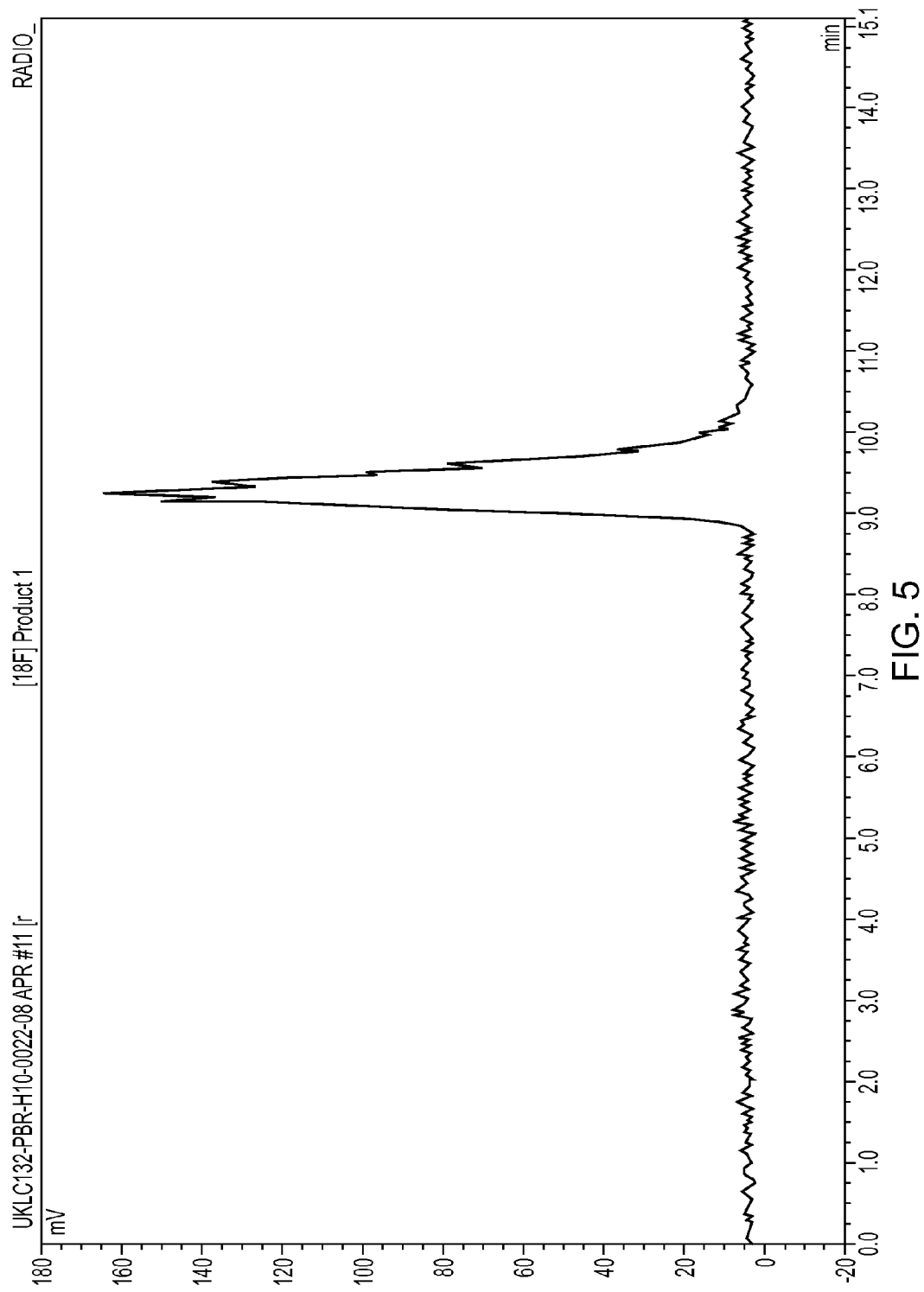

FIGS. 2 and 5 show the HPLC traces obtained using the above analytical achiral method for the PET tracer of the invention and its alternative enantiomer, respectively.

Analytical chiral HPLC was carried out as follows:

| | |
|---|---|
| 0-10 mins | 20%(B) |
| Column | Chiralpak IC 250 × 4.6 mm and Chiralpak IC guard column |
| Eluent | Methanol (pump A): Isopropyl alcohol(pump B) |
| Loop Size | 10 ul |
| Pump speed | 1 ml/min, |
| Wavelength | 220, 230 nm |

Figure 3:
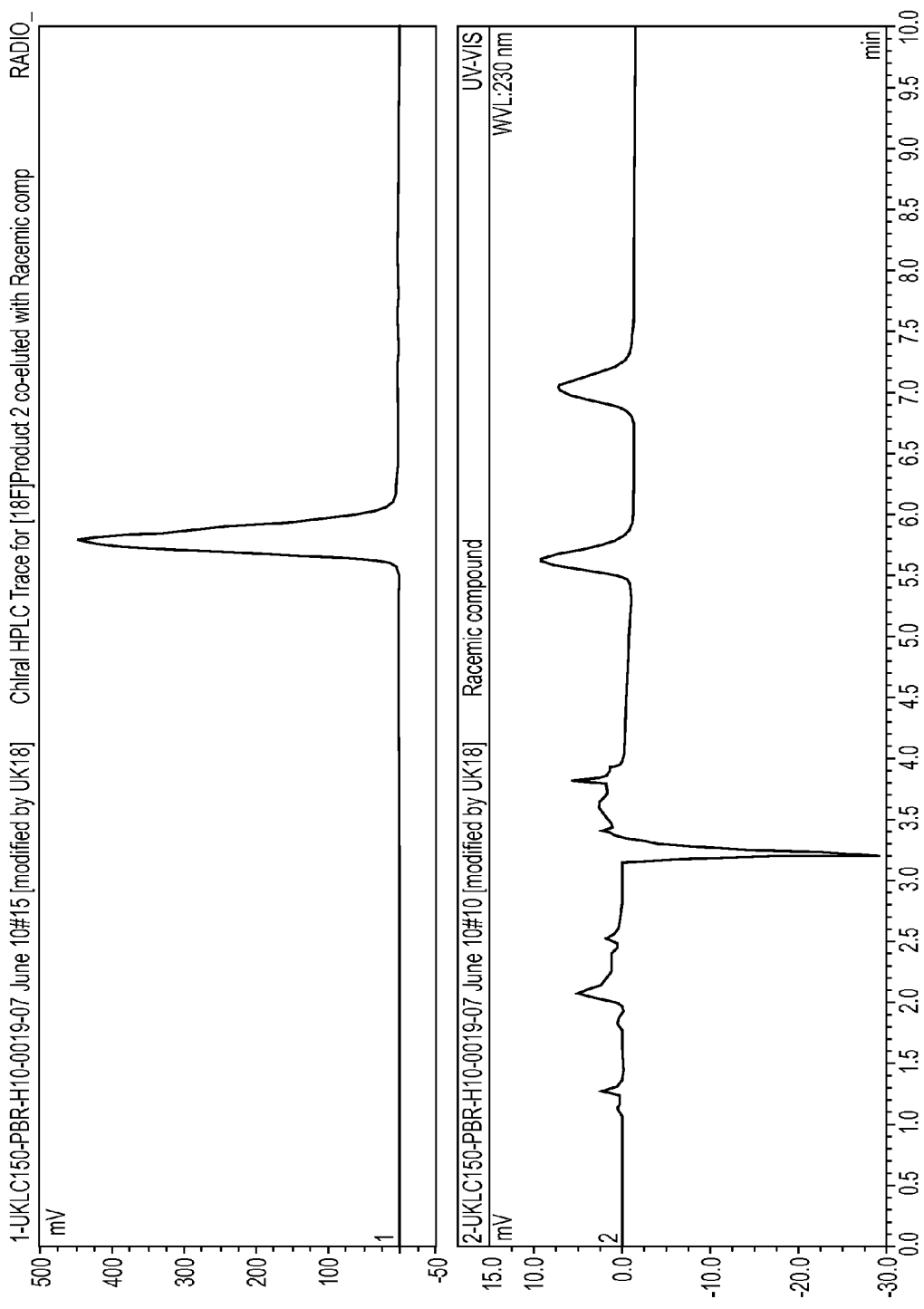
FIGS. 3 and 6 show HPLC traces obtained using a chiral HPLC method for the PET tracer of the invention and its alternative enantiomer, respectively.
Figure 6:
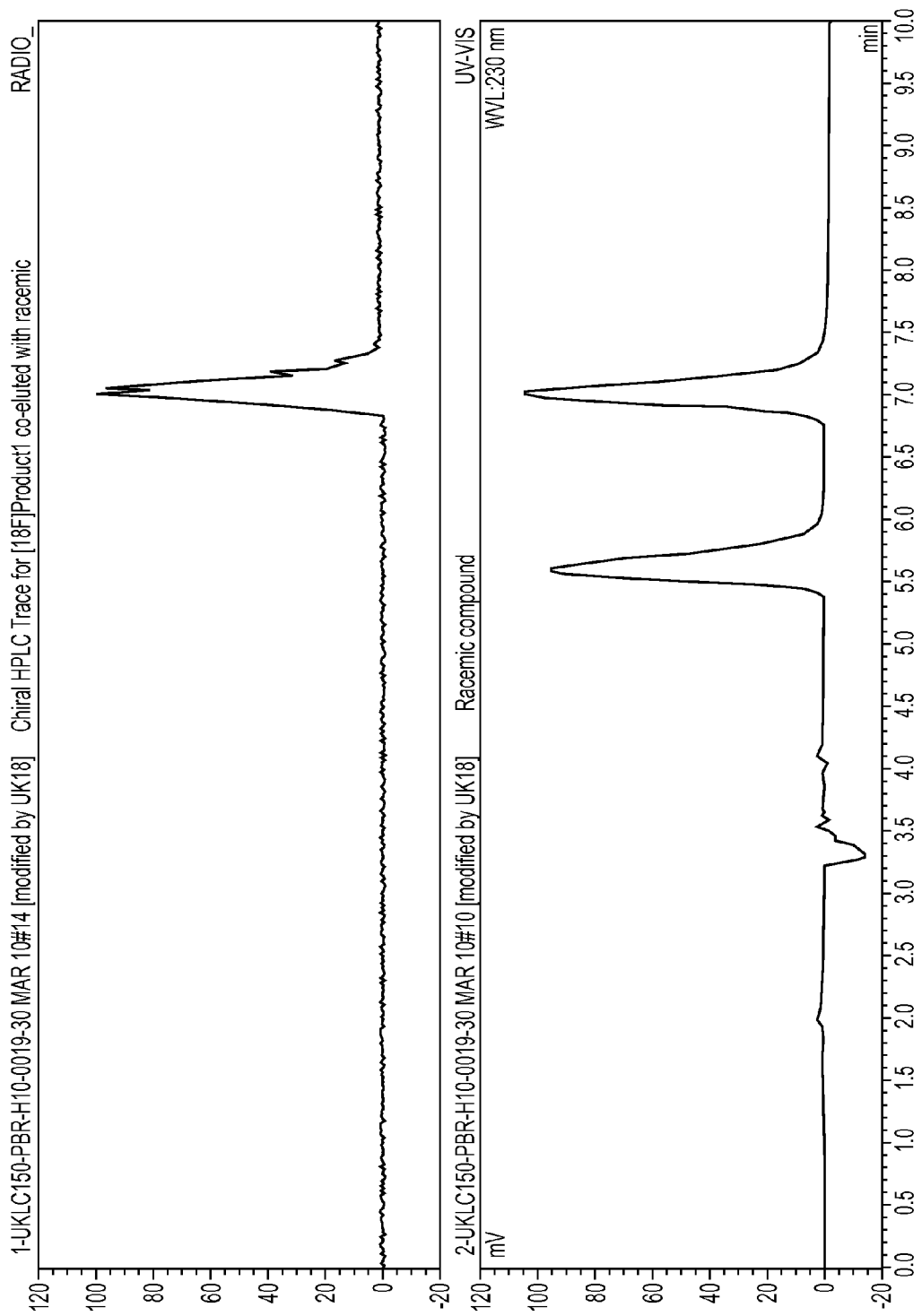

FIGS. 3 and 6 show the HPLC traces obtained using the above chiral HPLC method for the PET tracer of the invention and its alternative enantiomer, respectively.

The EOS yield for the PET tracer of the invention was 32%, and for its enantiomer was 19%.

Example 5

Synthesis of the Non-Radioactive Analogue of the PET Tracer of the Invention and Its Alternative Enantiomer

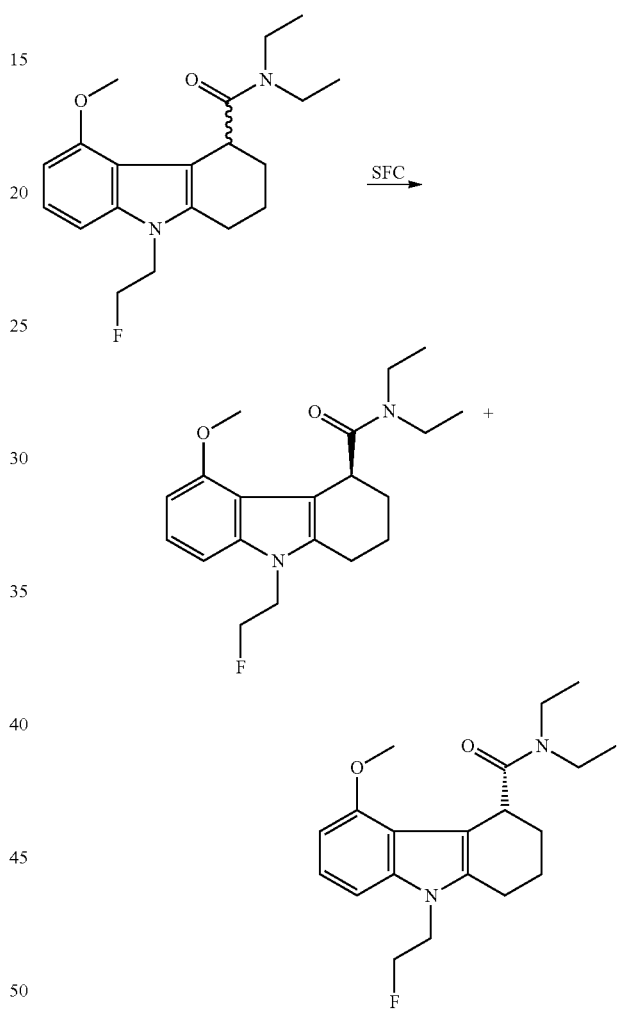

Non-radioactive PET Tracer

The racemic mixture of the non-radioactive PET tracer of the invention and its alternative enantiomer (obtained as described in Example 2) was separated into its enantiomers using chiral supercritical fluid (CO$_2$) chromatography (SFC) on a Kromasil Amycoat, 250×10 mm, 5 µm, 100 Å column using 20% IPA at 40° C. at 14 ml a min with a run time of 6 min. 100 mg of the racemic mixture was dissolved in 1.4-Dioxane (2.5 ml) and up to 200 µl at a time was as injected for each run. The fractions were cut by time to ensure that no mixed fractions were collected. Analytical HPLC determination of the enantiomeric purity of the two separated enantiomers on an IC from Chiral Technologies, 250×4.6 mm, 5 µm, run isocratic, 80:20—MeOH: IPA at 0.5 ml/min and room temperature indicated an enantiomeric purity of 99.5% of each of the enantiomers.

Example 6

Determination of Absolute Sterochemistry by Vibrational Circular Dichroism

The non-radioactive analogue of the PET tracer of the invention and its enantiomer, as well as Precursor Compound 1 and its enantiomer were tested. Each test compound was dissolved in $CDCl_3$ (5 mg/0.12 mL for the PET tracer and its enantiomer; 5 mg/0.15 mL for Precursor Compound 1 and its enantiomer) and placed in a 100 µm pathlength cell with $BaF_2$ windows. IR and VCD spectra were recorded on a Chiral/RTM VCD spectrometer (BioTools, Inc.) equipped with DualPEM accessory, with 4 $cm^{-1}$ resolution, 11 h collection for each sample, and instrument optimized at 1400 $cm^{-1}$. The IR of the solvent was collected for 150 scans. The solvent-subtracted IR and enantiomer-subtracted VCD spectra were collected. The optical rotation (OR) of each test compound was measured using a Jasco DIP-370 Polarimeter at 590 nm and 25° C.

| Test Compound | Optical Rotation (C = 0.33 in $CHCl_3$) |
| --- | --- |
| PET Tracer | −48.9° |
| Alternative Enantiomer of PET Tracer | +43.5° |
| Precursor Compound 1 | −52.2° |
| Alternative Enantiomer of Precursor Compound 1 | +50.1° |

The (R)-configuration in each case was built with Hyperchem (Hypercube, Inc., Gainesville, Fla.). A conformational search was carried out with Hyperchem for the entire structure at the molecular mechanics level. Geometry, frequency, and IR and VCD intensity calculations were carried out at the DFT level ($B_3LYP$ functional/6-31G(d) basis set) with Gaussian 09 (Gaussian Inc., Wallingford, Conn.). The calculated frequencies were scaled by 0.97 and the IR and VCD intensities were converted to Lorentzian bands with 6 $cm^{-1}$ half-width for comparison to experiment.

In respect of the PET Tracer and its enantiomer, Gaussian calculations of 36 conformers resulted in ten conformers that had energies within 1 kcal/mol from the lowest-energy conformer. The optimized geometries of the four lowest energy calculated conformers for the (R)-configuration were calculated, and the comparison of the observed VCD and IR spectra with those of the ten lowest energy calculated conformers was made. Based on the overall agreement in VCD pattern for the observed and the Botlzmann sum of the calculated spectra of the ten lowest energy conformers the absolute configuration of the non-radioactive analogue of the PET tracer of the invention is assigned as (S) and its enantiomer is assigned as (R). The assignment was evaluated by CompareVOA program (Biotools), and the confidence level of the assignment is 100% based on current database that includes 89 previous correct assignments for different chiral structures.

In respect of Precursor Compound 1 and its enantiomer, Gaussian calculations of 36 conformers resulted in 9 conformers that had energies within 1 kcal/mol from the lowest-energy conformer. Based on the overall agreement in VCD pattern for the observed and the Botlzmann sum of the calculated spectra of the nine lowest energy conformers the absolute configuration of precursor compound 1 is assigned as (S)- and its enantiomer is assigned as (R)-. The assignment was evaluated by CompareVOA program, and the confidence level of the assignment is 96% based on current database that includes 89 previous correct assignments for different chiral structures. This assignment is in agreement with the assignment of the configuration of the non-radioactive analogue of the PET tracer of the invention.

Example 7

In Vitro Potency Assay

Affinity for PBR was screened using a method adapted from Le Fur et al (Life Sci. 1983; USA 33: 449-57). Non-radioactive analogues of the PET tracer of the invention and the associated racemate were tested. Each test compound (dissolved in 50 mM Tris-HCl, pH 7.4, 10 mM $MgCl_2$ containing 1% DMSO) competed for binding to either Wistar rat heart PBR or human PBR against 0.3 nM [$^3$H] PK-11195. The reaction was carried out in 50 mM Tris-HCl, pH 7.4 10 mM $MgCl_2$ for 15 minutes at 25° C. Each test compound was screened at 6 different concentrations over a 300-fold range of concentrations around the estimated $K_i$. The following data were observed:

| Test Compound | Rat Heart Ki (nM) |
| --- | --- |
| PET Tracer of Invention | 0.87 |
| Racemate | 1.47 |
| Alternative Enantiomer | 3.87 |

| Test Compound | Human Ki (nM) |
| --- | --- |
| PET Tracer of Invention | 9.17 |
| Racemate | 11.5 |
| Alternative enantiomer | 14.1 |

Example 8

In Vitro Chiral Stability Assay

The non-radioactive PET tracer of the invention obtained according to Example 2 was incubated (37° C.) in human plasma or in rat liver $S_9$ fraction up to 4 hours. The enantiomers were extracted from the biological material by precipitation of proteins. The solid precipitate was separated from the liquid phase, which was evaporated to dryness. The dry residue was dissolved in acetonitrile.

A Dionex Ultimate 3000 HPLC system consisting of two pumps (micro pump LPG-3000 and Ultimate 3000 pump), a UV/visible detector, an auto sampler and two switching valves was applied in this study. One switching valve was connecting the two pumps and the auto sampler. This set-up made it possible to use either of the pumps to inject into the column. The pump used for injection was connected to the SPE column only. After the injection and elution the SPE column was washed using the injection pump. The system was made ready for a new injection while the chiral analysis was ongoing.

The other switching valve connected the analytical column and the SPE column. After the substance was retained on the SPE column the valve was switched and the analytical pump eluted the substance from the SPE column into the analytical chiral column. The flow direction of the elution was reversed to that of the retention. The analytical pump was connected to the analytical system only and was waiting for the analytes until the start of the elution. Both the run time of the retention on the SPE column and the elution time from this column were varied to optimize the two-step process.

Analytical column: Chiralpak IC 0.46×25 cm with the pre-column of same material 0.4×1 cm.

SPE column: LiChrospher ADS RP-4 25×4 mm (RAM column), 25 μm particles. MW cut-off: 15 kDa (Merck).

Mobile phase: A: Ammonium acetate 10 mM, pH 7; B: 1:1 MeCN:MeOH.

The flow was 300 μL/min.

Detection: UV-detection at 230 nm.

Retention on the SPE column: When retaining the analyte on the SPE column, isocratic mode using 10% MeCN in 50 mM ammonium acetate was applied. The retention lasted for 4 min and then the valve was switched.

Elution from the SPE column and separation: The elution started using mobile phase mixture of 10% MeCN and 90% 10 mM ammonium acetate. After 5 min the valve was switched back to the SPE column, which was washed with 90% MeCN/MeOH in buffer. The gradient on the analytical column started at 65% organic phase in buffer and was changed to 85% organic phase in buffer during 26.5 min. The analytical column was washed for 3 min using 70% MeCN/MeOH and then stabilized at 10% MeCN/MeOH to make the separation system ready for the next injection. The total run time was 40 min.

The PET tracer in plasma did not show any chromatographic changes after incubation for 4 hours. The chromatographic results were compared with a non-incubated sample in plasma and a reference solution of the PET tracer of the invention. No racemisation was observed.

The PET tracer of the invention in the rat liver $S_9$ fraction did not racemise after incubation for 4 hours.

Figure 7:
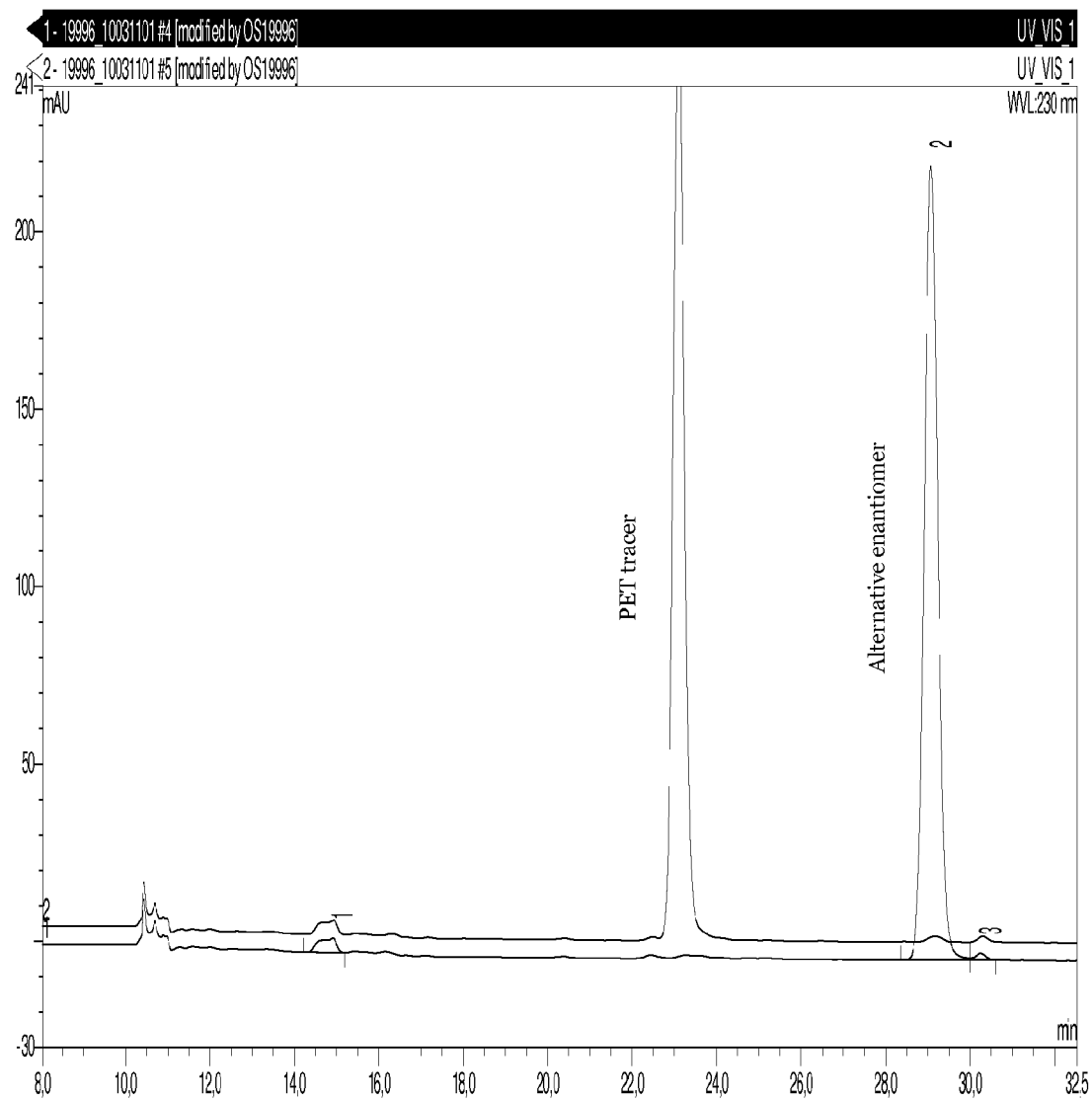
FIG. 7 shows overlay chromatograms of the PET tracer and alternative enantiomer, dissolved in acetonitrile at a concentration 0.1 mg/mL.

FIG. 7 shows overlay chromatograms of the PET tracer and alternative enantiomer, dissolved in acetonitrile at a concentration 0.1 mg/mL.

Figure 8A:
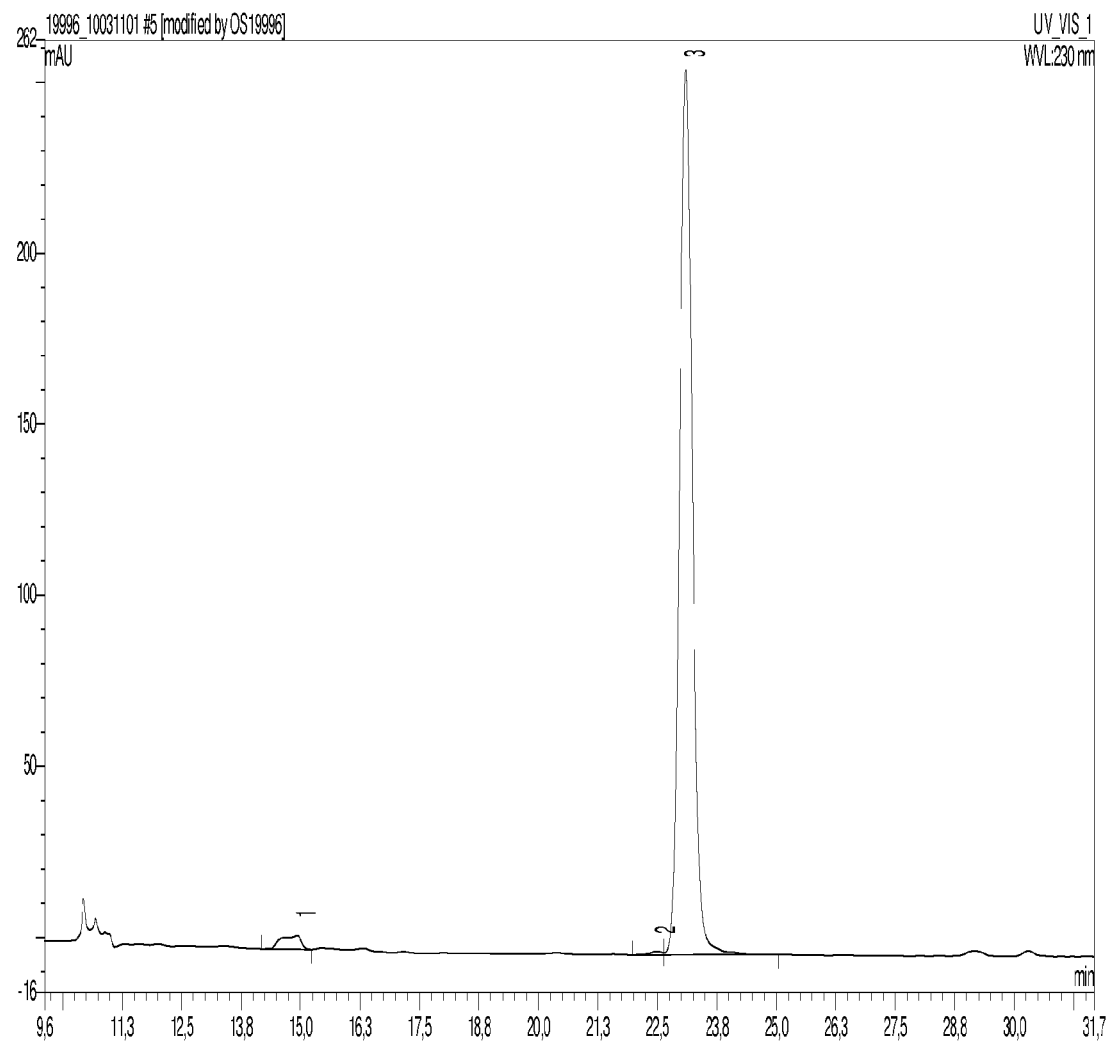
FIG. 8a shows a chromatogram of the PET tracer dissolved in acetonitrile at conc. 0.1 mg/mL.

FIG. 8a shows a chromatogram of the PET tracer dissolved in acetonitrile at conc. 0.1 mg/mL.

Figure 8B:
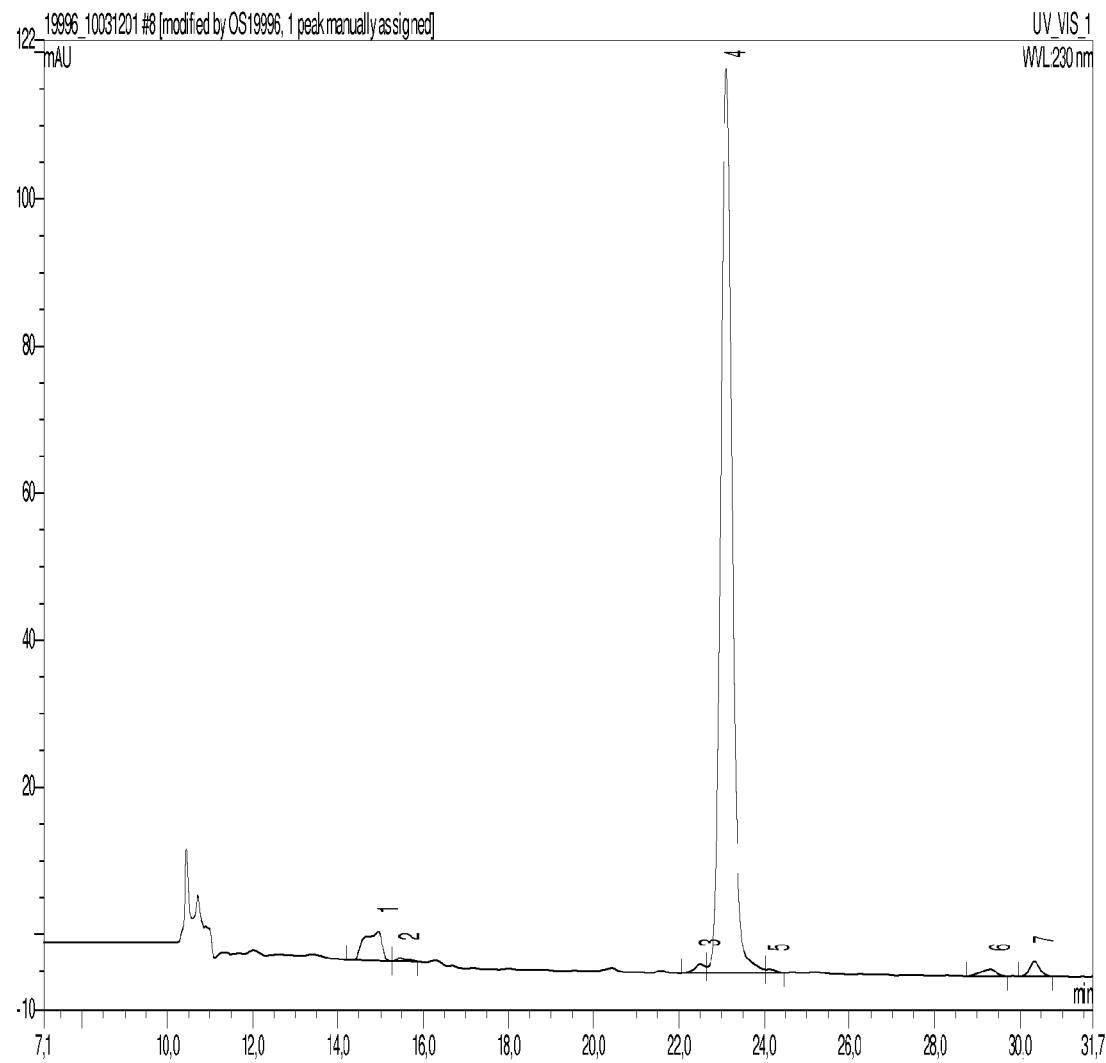
FIG. 8b shows a chromatogram of the PET tracer (0.1 mg/mL) added to human plasma and extracted prior to incubation.

FIG. 8b shows a chromatogram of the PET tracer (0.1 mg/mL) added to human plasma and extracted prior to incubation.

Figure 8C:
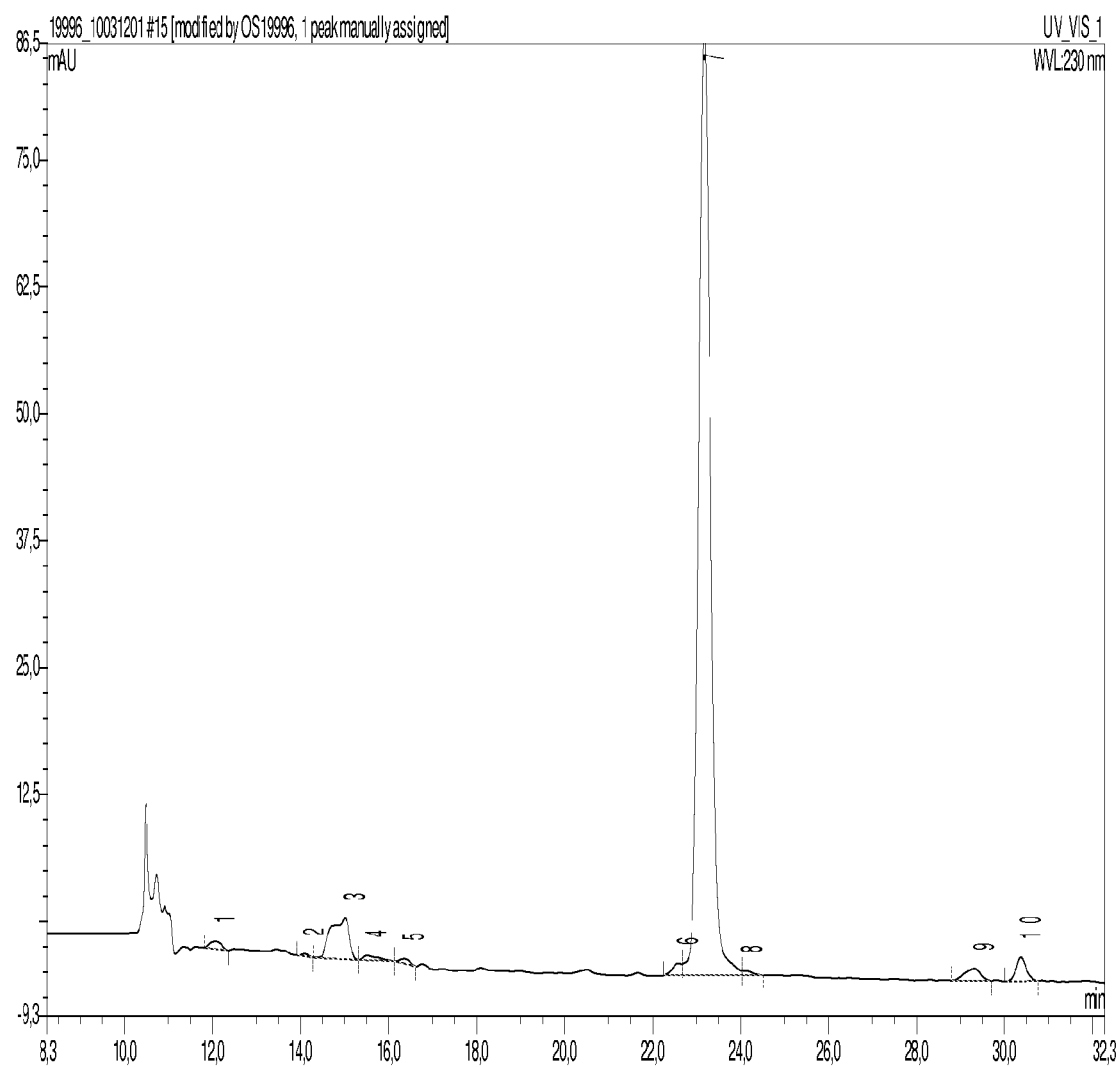
FIG. 8c shows a chromatogram of the PET tracer (0.1 mg/mL) incubated with human plasma and extracted.

FIG. 8c shows a chromatogram of the PET tracer (0.1 mg/mL) incubated with human plasma and extracted.

Example 9

In Vivo Biodistribution

The PET tracer of the invention, its alternative enantiomer, and the racemic mixture of the two, were tested in an in vivo biodistribution model.

Adult male Wistar rats (200-300 g) were injected with 1-3 MBq of test compound via the lateral tail vein. At 2, 10, 30 or 60 min (n=3) after injection, rats were euthanised and tissues or fluids were sampled for radioactive measurement on a gamma counter.

The following data of note were observed:

| Test Compound | Brain 2 min (% ID/g) | OB 30 min (% ID/g) | OB:Str 30 min |
| --- | --- | --- | --- |
| PET Tracer of Invention | 0.53 | 0.45 | 3.2 |
| Racemate | 0.52 | 0.36 | 3.0 |
| Alternative enantiomer | 0.53 | 0.23 | 2.9 |

Example 10

In Vivo Metabolism Study

The amount of brain or plasma activity that was due to parent test compound was tested up to 1 hour post-administration. The PET tracer of the invention and its associated racemate were the test compounds.

Adult male Wistar rats (150-200 g) were injected with approximately 20 MBq of test compound. Brain and plasma samples were analysed by HPLC at 10, 30 and 60 minutes pi. The following HPLC conditions were employed:

| Method: | Isocratic | |
| --- | --- | --- |
| Composition: | % Water (Buffer A) 60% | % Acetonitrile (Buffer B) 40% |
| Column: | Water's μBondapak C18 prep column | |
| Column Dimensions: | 7.8 × 300 mm; 10 μm; 125 A ° | |
| Flow Rate: | 3 ml/min | |
| Sample Injection Volume: | 1 ml | |

The following data of note were observed (wherein "pi" means post injection):

| | Brain (% parent) | | | Plasma (% parent) | | |
| --- | --- | --- | --- | --- | --- | --- |
| Test Compound | 10 min pi | 30 min pi | 60 min pi | 10 min pi | 30 min pi | 60 min pi |
| Racemate | 100 ± 0 | 97 ± 1 | 91 ± 2 | 81 ± 4 | 49 ± 12 | 28 ± 1 |
| PET Tracer of Invention | 98 ± 2 | 96 ± 2 | 94 ± 2 | 70 ± 18 | 41 ± 16 | 21 ± 5 |

Example 11

In Vivo Blocking Assay

The in vivo biodistributions of the PET tracer of the invention compared with its associated racemate were tested after pre-administration of their respective non-radioactive analogues, or pre-administration of the known PBR-specific ligand, PK11195.

Adult male Wistar rats (200-300 g) were injected with approximately 3-4 MBq of test compound via the lateral tail vein. PK11195 or a non-radioactive analogue (both at 3 mg/kg) was administered 5 min before the radiolabelled test compound. At 30 min after injection, rats were euthanised and tissues or fluids were sampled for radioactive measurement on a gamma counter.

The following data of note were observed:

| | Racemate (% of vehicle) | | PET Tracer of Invention (% of vehicle) | |
| --- | --- | --- | --- | --- |
| | PK11195 | Non-radioactive Analogue | PK11195 | Non-radioactive Analogue |
| Olfactory bulb | 37 | 59 | 43 | 37 |
| Striata | 114 | 124 | 117 | 114 |
| Blood | 247 | 289 | 289 | 253 |
| Lungs | 13 | 11 | 14 | 12 |
| Muscle | 90 | 140 | 131 | 143 |

Example 12

Facial Nerve Axotomy Model of Inflammation

Binding to a focal site of neuroinflammation was tested by autoradiography. The test compounds were the PET tracer of the invention and its associated racemate.

Male Wistar rats (200-300 g) were either used naïve, or underwent a facial nerve axotomy according to the procedure described by Graeber and Kreutzberg (J Neurocytol 1986; 15: 363-373). Various tissues including brain stem and olfactory bulb were removed from the animals and rapidly frozen in isopentane then stored at −70° C. until use. Tissues were sectioned (12 μm) and thaw-mounted onto Superfrost Plus slides. Slides were stored at −70° C. until use.

The slides were air dried prior to pre-incubation in Tris-HCl buffer (170 mM, pH 7.4) for 5 min at room temperature. 1000-fold excess of non-radioactive PK11195 at 1 μM, or non-radioactive PET tracer of the invention at 1 μM was added prior to incubation with Tris-HCl buffer (170 mM, pH 7.4) containing 8 GBq/ml of test compound for 60 minutes. The reaction was then terminated by rinsing the sections two times for 5 mins each in ice-cold buffer (Tris-HCl, 170 mM, pH 7.4) and then the slides were dipped briefly in distilled water to rinse. Next the slides were dried in air and exposed to x-ray film. When exposing to x-ray film, a reference standard was included, for in vitro autoradiography a reference sample (20μ) was taken from the solution and placed on filter paper (taped onto a glass) and exposed together with the sections. The film was exposed for 24 hours and the data were analysed by drawing regions of interest around the specific anatomic structures as well as around the blocked samples, references and background using MCID software using a density gradient scale as a calibration curve adjusted to the reference sample.

The following data of note were observed:

|  | Racemate (% specific binding) | | PET Tracer of Invention (% specific binding) | |
| --- | --- | --- | --- | --- |
|  | PK11195 | Unlabelled ligand | PK11195 | Unlabelled ligand |
| Olfactory bulb | 67 | 59 | 75 | 77 |
| Naïve brain stem | 13 | 21 | 70 | 70 |
| FNA brain stem | 69 | 72 | 86 | 86 |

The invention claimed is:

1. A positron-emission tomography (PET) tracer having the following chemical structure:

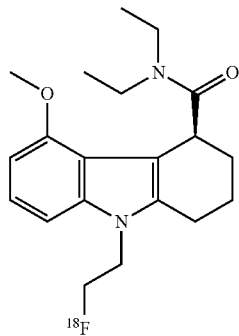

wherein the chiral centre has (S) configuration.

2. A radiopharmaceutical composition comprising the PET tracer according to claim 1 together with a biocompatible carrier.

3. A method to prepare the PET tracer according to claim 1 comprising the step of reacting a precursor compound of Formula I

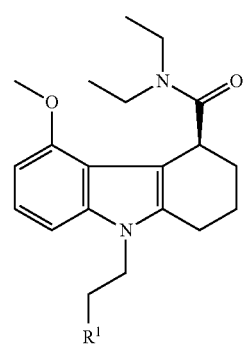

wherein $R^1$ is hydroxyl or is a leaving group selected from the group consisting of chloro, bromo, iodo, mesylate, tosylate, nosylate and triflate, with a suitable source of $^{18}F$; and wherein, optionally, the method is automated.

4. The method according to claim 3 wherein $R^1$ of said precursor compound of Formula I is a leaving group, and said suitable source of $^{18}F$ comprises $^{18}F$-fluoride and a cationic counterion.

5. The method according to claim 4 wherein said cationic counterion is selected from rubidium, caesium, potassium complexed by a cryptand, and a tetraalkylammonium salt.

6. A cassette for carrying out the method according to claim 3 comprising:
   i) a vessel containing said precursor compound; and
   ii) means for eluting said vessel of step (i) with said suitable source of $^{18}F$.

7. The cassette according to claim 6 which additionally comprises (iii) an ion-exchange cartridge for removal of excess $^{18}F$.

8. A precursor compound of Formula I:

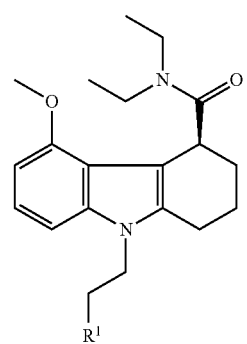

wherein $R^1$ is hydroxyl or is a leaving group selected from the group consisting of chloro, bromo, iodo, mesylate, tosylate, nosylate and triflate.

9. The precursor compound according to claim 8 wherein said leaving group is selected from the group consisting of mesylate, tosylate and triflate.

10. The precursor compound according to claim 9 wherein said leaving group is mesylate.

11. A method to prepare the precursor compound of Formula I according to claim 8 comprising the steps of:
  (i) providing a racemic mixture of said precursor compound of Formula I (I)

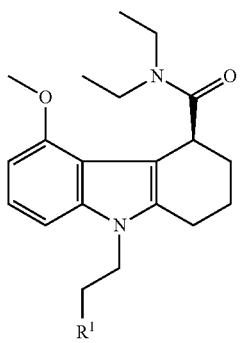

wherein R¹ is hydroxyl or is a leaving group selected from the group consisting of chloro, bromo, iodo, mesylate, tosylate, nosylate and triflate,
and a compound of Formula II:

(II)

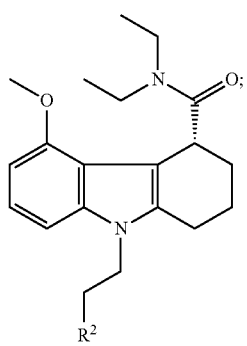

wherein R² is as defined for R¹ above and R¹ and R² are the same; and
  (ii) separating said precursor compound of Formula I from said compound of Formula II.

12. The method according to claim 11 wherein said separating step (ii) is achieved by at least one of the following separation techniques: high performance liquid chromatography, supercritical fluid chromatography, and simulated bed chromatography.

13. A method to prepare the precursor compound of Formula I according to claim 8 comprising the steps of:
  (i) providing a compound of Formula III:

(III)

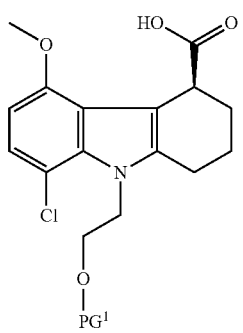

wherein PG¹ is a hydroxyl protecting group;

(ii) converting said compound of Formula III to its corresponding acid chloride;
  (iii) reacting the acid chloride obtained in step (ii) with diethylamide to obtain a compound of Formula IV:

(IV)

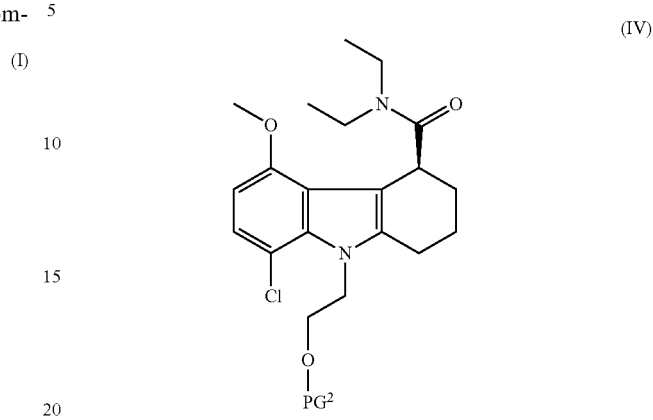

wherein PG² is a hydroxyl protecting group and is the same as PG¹; and
  (iv) deprotecting the compound of Formula IV obtained in step (iii) to obtain the hydroxyl derivative; or
  (v) adding a leaving group selected from the group consisting of chloro, bromo, iodo, mesylate, tosylate, nosylate and triflate.

14. The method according to claim 13 wherein said providing step (i) comprises:
  (a) providing an equimolar mixture of a compound of Formula V and a compound of Formula VI:

(V)

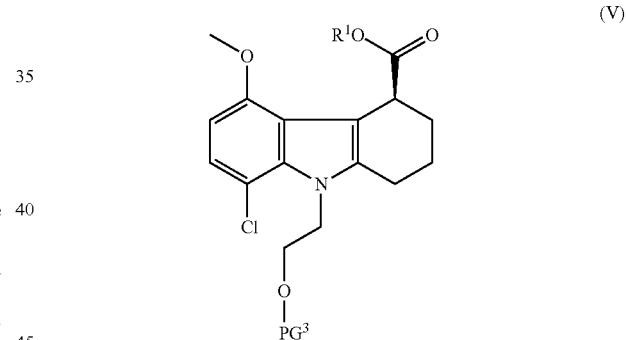

(VI)

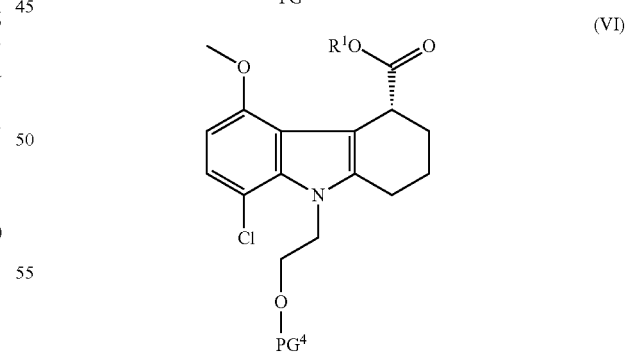

wherein:
R¹ is a chiral alcohol; and,
PG³ and PG⁴ are the same and are each a hydroxyl protecting group;
  (b) separating the compound of Formula V from the compound of Formula VI; and
  (c) removing R¹ from the separated compound of Formula V using acidic conditions to provide said compound of Formula III.

15. The method according to claim 13 wherein said providing step (i) comprises:
(a) providing a racemic mixture of said compound of Formula III and a compound of Formula VIII:

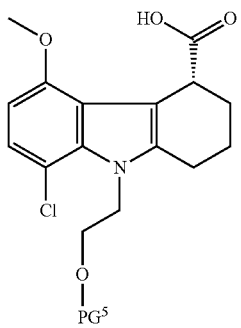

(VIII)

wherein $PG^5$ and $PG^1$ of said compound of Formula III are the same and are each a hydroxyl protecting group;
(b) reacting said racemic mixture with an optically active amine; and
(c) separating said compound of Formula III from said compound of Formula VIII.

16. The method according to claim 15 wherein said optically active amine is selected from the group consisting of S-Alpha-MethylBenzylamine, R-(+)-N-(1-Naphthylmethyl)-Alpha-Benzylamine, N-(2-Hydroxy)ethyl-Alpha-methyl benzyl amine, and 1(P-Tolyl) Ethylamine.

17. The method according to claim 13 wherein said providing step (i) comprises:
(a) providing a racemic mixture of a compound of Formula IX and a compound of Formula X:

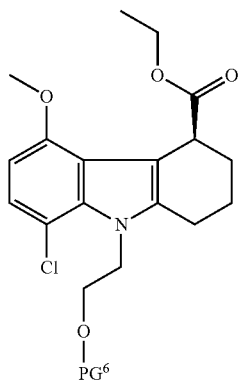

(IX)

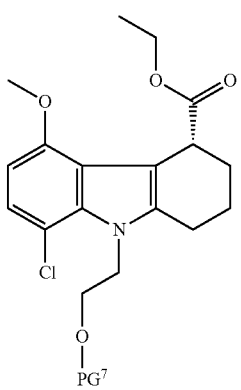

(X)

wherein $PG^6$ and $PG^7$ are the same and are each a hydroxyl protecting group;
(b) reacting said racemic mixture with a stereo selective enzyme to obtain said compound of Formula III wherein said stereo selective enzyme effects ester hydrolysis of the compound of Formula IX.

18. The method as defined in claim 17 wherein said stereo selective enzyme is at least one selected from the group consisting of *Candida antarctica* lipase B, porcine liver esterase and porcine pancreatic lipase.

19. A PET imaging method to determine the distribution and/or the extent of PBR expression in a subject, wherein said method comprises:
i) administering to said subject the PET tracer as defined in claim 1;
ii) allowing said PET tracer to bind to PBR in said subject;
iii) detecting signals emitted by the $^{18}F$ comprised in said bound PET tracer;
iv) generating an image representative of the location and/or amount of said signals; and,
v) determining the distribution and extent of PBR expression in said subject wherein said expression is directly correlated with said signals.

20. The PET imaging method according to claim 19 wherein said PET tracer is administered as a radiopharmaceutical composition comprising said PET tracer together with a biocompatible carrier.

* * * * *